United States Patent
Garraway et al.

(10) Patent No.: US 9,880,169 B2
(45) Date of Patent: Jan. 30, 2018

(54) MEK1 MUTATION CONFERRING RESISTANCE TO RAF AND MEK INHIBITORS

(71) Applicants: Levi A. Garraway, Newton, MA (US); Caroline Emery, Cambridge, MA (US); Nikhil Wagle, Brookline, MA (US)

(72) Inventors: Levi A. Garraway, Newton, MA (US); Caroline Emery, Cambridge, MA (US); Nikhil Wagle, Brookline, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 15/011,003

(22) Filed: Jan. 29, 2016

(65) Prior Publication Data

US 2016/0216266 A1    Jul. 28, 2016

Related U.S. Application Data

(63) Continuation of application No. 13/701,889, filed as application No. PCT/US2011/039789 on Jun. 9, 2011, now abandoned.

(60) Provisional application No. 61/352,959, filed on Jun. 9, 2010.

(51) Int. Cl.
| G01N 33/573 | (2006.01) |
| G01N 33/574 | (2006.01) |
| C12N 9/12 | (2006.01) |
| C12Q 1/68 | (2006.01) |

(52) U.S. Cl.
CPC ....... *G01N 33/5743* (2013.01); *C12N 9/1205* (2013.01); *C12Q 1/6886* (2013.01); *C12Y 207/12002* (2013.01); *C12Q 2600/106* (2013.01); *C12Q 2600/136* (2013.01); *C12Q 2600/156* (2013.01); *G01N 2333/91205* (2013.01); *G01N 2500/10* (2013.01); *G01N 2500/20* (2013.01)

(58) Field of Classification Search
None
See application file for complete search history.

(56) References Cited

U.S. PATENT DOCUMENTS

| 4,582,788 A | 4/1986 | Erlich |
| 4,656,127 A | 4/1987 | Mundy |
| 4,659,774 A | 4/1987 | Webb et al. |
| 4,682,195 A | 7/1987 | Yilmaz |
| 4,683,194 A | 7/1987 | Saiki et al. |
| 4,683,202 A | 7/1987 | Mullis |
| 4,684,611 A | 8/1987 | Schilperoort et al. |
| 4,816,571 A | 3/1989 | Andrus et al. |
| 4,879,236 A | 11/1989 | Smith et al. |
| 4,946,773 A | 8/1990 | Maniatis et al. |
| 4,952,500 A | 8/1990 | Finnerty et al. |
| 4,959,463 A | 9/1990 | Froehler et al. |
| 5,096,676 A | 3/1992 | McPherson et al. |
| 5,141,813 A | 8/1992 | Nelson |
| 5,223,409 A | 6/1993 | Ladner et al. |
| 5,264,566 A | 11/1993 | Froehler et al. |
| 5,302,523 A | 4/1994 | Coffee et al. |
| 5,322,783 A | 6/1994 | Tomes et al. |
| 5,384,253 A | 1/1995 | Krzyzek et al. |
| 5,419,278 A | 5/1995 | Carter |
| 5,428,148 A | 6/1995 | Reddy et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,554,744 A | 9/1996 | Bhongle et al. |
| 5,563,055 A | 10/1996 | Townsend et al. |
| 5,574,146 A | 11/1996 | Reddy et al. |
| 5,580,859 A | 12/1996 | Felgner et al. |
| 5,589,466 A | 12/1996 | Felgner et al. |
| 5,591,616 A | 1/1997 | Hiei et al. |
| 5,602,244 A | 2/1997 | Caruthers et al. |
| 5,610,042 A | 3/1997 | Chang et al. |
| 5,645,897 A | 7/1997 | Andra |
| 5,650,298 A | 7/1997 | Bujard et al. |
| 5,656,610 A | 8/1997 | Shuler et al. |
| 5,702,932 A | 12/1997 | Hoy et al. |
| 5,705,629 A | 1/1998 | Bhongle |
| 5,736,524 A | 4/1998 | Content et al. |
| 5,780,448 A | 7/1998 | Davis |
| 5,789,215 A | 8/1998 | Berns et al. |

(Continued)

FOREIGN PATENT DOCUMENTS

| EP | 0 050 424 A1 | 4/1982 |
| EP | 0 084 796 B1 | 8/1983 |
| EP | 0 201 184 A2 | 12/1986 |
| EP | 0 237 362 A1 | 9/1987 |
| EP | 0 266 032 A1 | 5/1988 |
| EP | 1 078 985 A2 | 2/2001 |
| EP | 0 258 017 B2 | 12/2004 |
| FR | 2 650 840 A1 | 2/1991 |
| WO | WO 91-02087 A1 | 2/1991 |
| WO | WO 92-15712 A1 | 9/1992 |
| WO | WO 94-09699 A1 | 5/1994 |
| WO | WO 95-06128 A2 | 3/1995 |
| WO | WO 2005/034840 A2 | 4/2005 |
| WO | WO 2006-024836 A1 | 3/2006 |
| WO | WO 2008-020203 A1 | 2/2008 |
| WO | WO 2008-028141 A2 | 3/2008 |
| WO | WO 2010-068738 A1 | 6/2010 |

OTHER PUBLICATIONS

Translation of Office Action dated Feb. 3, 2017 for Japanese Patent Application No. JP 2016-056541.

(Continued)

*Primary Examiner* — Lei Yao
(74) *Attorney, Agent, or Firm* — Brinks Gilson & Lione

(57) ABSTRACT

Nucleic acids and proteins having a mutant MEK sequence, and methods concerning identification of patients having resistance to treatment with anti-cancer agents, specifically inhibitors of RAF or MEK are provided. Methods of treatment and for optimizing treatment for patients having a mutation in a MEK1 sequence are also provided.

3 Claims, 4 Drawing Sheets

(56) References Cited

U.S. PATENT DOCUMENTS

| | | | |
|---|---|---|---|
| 5,849,483 | A | 12/1998 | Shuber |
| 5,851,770 | A | 12/1998 | Babon et al. |
| 5,866,337 | A | 2/1999 | Schon |
| 5,871,986 | A | 2/1999 | Boyce |
| 5,925,525 | A | 7/1999 | Fodor et al. |
| 5,928,870 | A | 7/1999 | Lapidus et al. |
| 5,945,100 | A | 8/1999 | Fick |
| 5,952,174 | A | 9/1999 | Nikiforov et al. |
| 5,981,274 | A | 11/1999 | Tyrrell et al. |
| 5,994,624 | A | 11/1999 | Trolinder et al. |
| 6,054,273 | A | 4/2000 | Housman |
| 6,200,754 | B1 | 3/2001 | Housman et al. |
| 6,296,673 | B1 | 10/2001 | Santarsiero et al. |
| 2005/0084905 | A1* | 4/2005 | Prescott .................. C12Q 1/485 435/7.1 |

OTHER PUBLICATIONS

Bindslev, L., "Full=Mitogen-activated protein kinase kinase—Blumeria graminis"; Nucleotide Sequence, XP-002657036; Dept. of Molecular Biology, University of Copenhagen, Copenhagen, Denmark; Mar. 2001; 1 page.

Bindslev, L.; "Blumeria graminis bekl gene for mitogen-activated protein kinase kinase"; Nucleotide Sequence; XP-002657037; Dept. of Molecular Biology, University of Copenhagen, Copenhagen, Denmark; Dec. 2000; 1 page.

Boobbyer, D. N. A. et al., "New Hydrogen-Bond Potentials for Use in Determining Energetically Favorable Binding Sites on Molecules of Known Structure," Journal of Medical Chemistry, vol. 32, No. 5, 1989, pp. 1083-1094.

Brünger A. T. et al, "Solution of a Protein Crystal Structure with a Model Obtained from NMR Interproton Distance Restraints," Science, vol. 235, 1987, pp. 1049-1053.

Brünger A. T. et al., "Crystallography & NMR System: A New Software Suite for Macromolecular Structure Determination," Acta Crystallography, vol. D54, 1998, pp. 905-921.

Carbonelli, D. L. et al., "A Plasmid Vector for Isolation of Strong Promoters in Escherichia coli," FEMS Microbiology Letters, vol. 177, 1999, pp. 75-82.

Carell, T. et al., "A Novel Procedure for the Synthesis of Libraries Containing Small Organic Molecules," Angewandte Chemie International Edition Engl., vol. 33, No. 20, 1994, pp. 2059-2061.

Carell T. et al., "A Solution-Phase Screening Procedure for the Isolation of Active Compounds from a Library of Molecules," Angewandte Chemie International Edition Engl., vol. 33, No. 20, 1994, pp. 2061-2064.

Chandler, S. D. et al., "RNA Splicing Specificity Determined by the Coordinated Action of RNA Recognition Motifs in SR Proteins," Proceedings of the National Academy of Sciences of the United States of America, vol. 94, 1997, pp. 3596-3601.

Chen, C. et al., "High-Efficiency Transformation of Mammalian Cells by Plasmid DNA," Molecular and Cellular Biology, vol. 7, No. 8, 1987, pp. 2745-2752.

Chou Ting-Chao et al., "Quantitative analysis of dose-effect relationships: the combined effects of multiple drugs of enzyme inhibitors," Advances in Enzyme Regulation, vol. 22, 1984, pp. 27-55.

Cocea, L. "Duplication of a Region in the Multiple Cloning Site of a Plasmid Vector to Enhance Cloning-Mediated Addition of Restriction Sites to a DNA Fragment," BioTechniques, vol. 23, No. 5, 1997, pp. 814-816.

Cull, M. G. et al., "Screening for receptor ligands using large libraries of peptides linked to the C terminus of the lac repressor," Proceedings of the National Academy of Sciences of the United States of America, vol. 89, 1992, pp. 1865-1869.

Cwirla, S. E. et al., "Peptides on Phage: A Vast Library of Peptides for Identifying Ligands," Proceedings of the National Academy of Sciences of the United States of America, vol. 87, 1990, pp. 6378-6382.

DesJarlias, R. L. et al., "Using Shape Complemenarity as an Initial Screen in Designing Lignads for a Receptor Binding Site of Known Three-Dimensional Structure," Journal of Medicinal Chemistry, vol. 31, No. 4, 1988, pp. 722-729.

Devlin, J. J. et al., "Random Peptide Libraries: A Source of Specific Protein Binding Molecules," Science, vol. 249, 1990, pp. 404-406.

Drenth, J., Ch. 1, "Crystallizing a Protein," Principles of Protein X-ray Crystallography, New York: Springer-Verlag, copyright 1994, pp. 1-19.

Drmanac, RT et al.; "Novel human diagnostic protein #28203"; Nucleotide Sequence; XP-002657038; Hyseq, Inc.; Feb. 2002; 1 page.

Emery, Caroline M. et al., "MEK1 mutations confer resistance to MEK and B-RAF inhibiton," Proc. Natl. Acad. Sci. USA, vol. 106, No. 48, Dec. 2009, pp. 20411-20416.

Erb, E. et al., "Recursive Deconvolution of Combinatorial Chemical Libraries," Proceedings of the National Academy of Sciences of the United States of America, vol. 91, 1994, pp. 11422-11426.

Fechheimer, M. et al., "Transfection of Mammalian Cells with Plasmid DNA by Scrape Loading and Sonication Loading," Proceedings of the National Academy of Sciences of the United States of America, vol. 84, 1987, pp. 8463-8467.

Felici, F. et al., "Selection of Antibody Ligands from a Large Library of Oligopeptides Expressed on a Multivalent Exposition Vector," Journal of Molecular Biology, vol. 222, 1991, pp. 301-310.

Fodor, S. P. A. et al., "Multiplexed Biochemical Assays with Biological Chips," Nature, vol. 364, 1993, pp. 555-556.

Fraley, R. T. et al., "Entrapment of a Bacterial Plasmid in Phospholipid Vesicles: Potential for Gene Transfer," Proceedings of the National Academy of Sciences of the United States of America, vol. 76, No. 7, 1979, pp. 3348-3352.

Friday, Bret B. et al., "Advances in Targeting the Ras/Raf/MEK/Erk Mitogen-Activated Protein Kinase Cascade with MEK Inhibitors for Cancer Therapy," Molecular Pathways, Clinical Cancer Research, vol. 14(2), Jan. 2008, pp. 342-346.

Froehler, B. C. et al., "Synthesis of DNA Via Deoxynucleoside H-phosphonate Intermediates," Nucleic Acids Research, vol. 14, No. 13, 1986, pp. 5399-5407.

Gallop, M. A. et al., "Applications of Combinatorial Technologies to Drug Discovery. 1. Background and Peptide Combinatorial Libraries," Journal of Medical Chemistry, vol. 37, No. 9, 1994, pp. 1233-1251.

Geromichalos, G. D., "Importance of Molecular Computer Modeling in Anitcancer Drug Development," Journal of Balkan Union of Oncology (BUON), vol. 12, Suppl. 1, 2007, pp. S101-S118.

Gnirke, Andreas et al., "Solution Hybrid Selection with Ultra-long Oligonucleotides for Massively Parallel Targeted Sequencing," Nat. Biotechnol., vol. 27(2), Feb. 2009, pp. 182-189.

Goodford, P. J. et al., "A Computational Procedure for Determining Energetically Favorable Binding Sites on Biologically Important Macromolecules," (1985) Journal of Medicinal Chemistry, vol. 28, pp. 849-857.

Gopal, T. V., "Gene Transfer Method for Transient Gene Expression, Stable Transformation, and Cotransformation of Suspension Cell Cultures," Molecular and Cellular Biology, vol. 5, No. 5, 1985, pp. 1188-1190.

Gossen, M. et al., "Tight control of gene expression in mammalian cells by tetracycline-responsive promoters," Proceedings of the National Academy of Sciences of the United States of America, vol. 89, 1992, pp. 5547-5551.

Gossen, M. et al., "Transcriptional Activation by Tetracyclines in Mammalian Cells," Science, vol. 268, 1995, pp. 1766-1769.

Graham, F. L. et al., "A New Technique for the Assay of Infectivity of Human Adenovirus 5 DNA," Virology, vol. 52, 1973, pp. 456-467.

Harland, R. et al., "Translation of mRNA Injected into Xenopus Oocytes Is Specifically Inhibited by Antisense RNA," Journal of Cell Biology, vol. 101, 1985, pp. 1094-1099.

Ho, C. M. W. et al., "Cavity Search: An Algorithm for the Isolation and Display of Cavity-Like Binding Regions," Journal of Computer-Aided Molecular Design, vol. 4, 1990, pp. 337-354.

(56) References Cited

OTHER PUBLICATIONS

Holford, Nicholas H.G. et al., "Understanding the Dose-Effect Relationship: Clinical Application of Pharmacokinetic-Pharmacodynamic Models," Clinical Pharmacokinetics, vol. 6, 1981, pp. 429-453.
Harwell, D. et al., "'Targeted' Molecular Diversity: Design and Development of Non-Peptide Antagonists for Cholecystokinin and Tachykinin Receptors," Immunopharmacology, vol. 33, 1996, pp. 68-72.
Houghten, R. A. et al., "The Use of Synthetic Peptide Combinatorial Libraries for the Identification of Bioactive Peptides," BioTechniques, vol. 13, No. 3, 1992, pp. 412-421.
Kaeppler H. F. et al., "Silicon Carbide Fiber-Mediated DNA Delivery Into Plant Cells," Plant Cell Reports, vol. 9, 1990, pp. 415-418.
Kaneda, Y. et al., "Increased Expression of DNA Cointroduced with Nuclear Protein in Adult Rat Liver," Science, vol. 243, 1989, pp. 375-378.
Kato, K. et al., "Expression of Hepatitis B Virus Surface Antigen in Adult Rat Liver," Journal of Biological Chemistry, vol. 266, No. 6, 1991, pp. 3361-3364.
Kornher, J. S. et al., "Mutation Detection Using Nucleotide Analogs that Alter Electrophoretic Mobility," Nucleic Acids Research, vol. 17, No. 19, 1989, pp. 7779-7784.
Kuppuswamy, M. N. et al., "Single Nucleotide Primer Extension to Detect Genetic Diseases: Experimental Application to Hemophilia B (Factor IX) and Cystic Fibrosis Genes," Proceedings of the National Academy of Sciences of the United States of America, 1991, vol. 88, pp. 1143-1147.
Lam, K.S. et al., "A New Type of Synthetic Peptide Library for Identifying Ligand-Binding Activity," Nature, vol. 354, 1991, pp. 82-84.
Lam, K.S., Abstract of "Application of Combinatorial Library Methods in Cancer Research and Drug Discovery," Anticancer Drugs Design, vol. 12, No. 3, 1997, pp. 145-167.
Landegren et al., "A Ligase-Mediated Gene Detection Technique," Science, vol. 241, 1988, pp. 1077-1080.
Lawrence, Davis, "CLIX: A Search Algorithm for Finding Novel Ligands Capable of Binding Proteins of Known Three-Dimensional Structure," Proteins, Jan. 1992, vol. 12(1), pp. 31-41 (Abstract only), 1 page.
Levenson, V. V. et al., "Internal Ribosomal Entry Site-Containing Retroviral Vectors with Green Fluorescent Protein and Drug Resistance Markers," Human Gene Therapy, vol. 9, 1998, pp. 1233-1236.
Loewe, S. et al., Arch. Exp. Pathol. Pharmaco., vol. 114, 1926, pp. 313-326.
Mallon, Robert et al., "Identification of 4-anilino-3-quinolinecarbonitrile inhibitors of mitogen-activated protein/extracellular signal-regulated kinase 1 kinase," Molecular Cancer Therapeutics, vol. 3(6), Jun. 2004, pp. 755-762.
Marks, Jenifer L. et al., "Novel *MEK1* Mutation Identified by Mutational Analysis of Epidermal Growth Factor Receptor Signaling Pathway Genes in Lung Adenocarcinoma," Cancer Research, vol. 68(14), Jul. 2008, pp. 5524-5528.
Maxam, A. M., et al., "A New Method for Sequencing DNA," Proceedings of the National Academy of Sciences of the United States of America, vol. 74, No. 2, 1977, pp. 560-564.
Meng, E. C. et al., "Automated Docking with Grid-Based Energy Evaluation," Journal of Computational Chemistry, vol. 13, No. 4, 1992, pp. 505-524.
Meng, E. C. et al., "Orientational Sampling and Rigid-Body Minimization in Molecular Docking," Proteins: Structure, Function, and Genetics, vol. 17, 1993, pp. 266-278.
Mullis, K. et al., "Specific Enzymatic Amplification of DNA in Vitro: The Polymerase Chain Reaction," Cold Spring Harbor Symposia on Quantitative Biology, vol. 51, 1986, pp. 263-273.

Narula, S. S. et al., "Solution structure of the C-terminal SH2 domain of the human tyrosine kinase Syk complexed with a phosphotyrosine pentapeptide," Structure, vol. 3, No. 10, 1995, pp. 1061-1073.
Nickerson, D. A. et al., "Automated DNA Diagnostics Using an ELISA-based Oligonucleotide Ligation Assay," Proceedings of the National Academy of Sciences of the United States of America, vol. 87, 1990, pp. 8923-8927.
Nicolau, C. et al., "Liposome-Mediated DNA Transfer in Eukaryotic Cells. Dependence of the Transfer Efficiency Upon the Type of Liposomes Used and the Host Cell Cycle Stage," Biochimica et Biobhysica Acta, vol. 721, 1982, pp. 185-190.
Nicolau, C. et al., "Liposomes as Carriers for in Vivo Gene Transfer and Expression," Methods in Enzymology, vol. 149, 1987, pp. 157-176.
Nyrén, P. et al., "Solid Phase DNA Minisequencing by an Enzymatic Luminometric Inorganic Pryophosphate Detection Assay," Analytical Biochemistry, vol. 208, 1993, pp. 171-175.
Omirulleh, S. et al., "Activity of a Chimeric Promoter with the Doubled CaMV 35S Enhancer Element in Protoplast-Derived Cells and Transgenic Plains in Maize," Plant Molecular Biology, vol. 21, 1993, pp. 415-428.
Potrykus, I. et al., "Molecular and General Genetics of a Hybrid Foreign Gene Introduced into Tobacco by Direct Gene Transfer," Molecular and General Genetics, vol. 199, 1985, pp. 169-177.
Prezant, T. R. et al., "Trapped-Oligonucleotide Nucleotide Incorporation (TONI) Assay, a Simple Method for Screening Point Mutations," Human Mutation, vol. 1, 1992, pp. 159-164.
Rippe, R. A. et al., "DNA-Mediated Gene Transfer into Adult Rat Hepatocytes in Primary Culture," Molecular and Cellular Biology, vol. 10, No. 2, 1990, pp. 689-695.
Sanger, F., et al., Abstract of "A Rapid Method for Determining Sequences in DNA by Primed Synthesis with DNA Polymerase," Journal of Molecular Biology, vol. 94, No. 3, 1975, pp. 441-446.
Scott, J. K., et al., "Searching for Peptide Ligands with an Epitope Library," Science, 1990, vol. 249, pp. 386-390.
Shoichet, B. K. et al., "Structure-Based Discovery of Inhibitors of Thymidylate Synthase," Science, 1993, vol. 259, pp. 1445-1450.
Sokolov, B. P., "Primer Extension Technique for the Detection of Single Nucleotide in Genomic DNA," Nucleic Acids Research, vol. 18, No. 12, 1989, pp. 3671.
Stevens, R. C. et al., "High-throughput protein crystallization," Current Opinion in Structural Biology, vol. 10, 2000, pp. 558-563.
Syvänen, Ann-Christine et al., "A Primer-Guided Nucleotide Incorporation Assay in the Genotyping of Apolipoprotein E," Genomics, vol. 8, 1990, pp. 684-692.
Syvänen, A-C. et al., "Identification of Individuals by Analysis of Biallelic DNA Markers, Using PCR and Solid-Phase Minisequencing," American Journal of Human Genetics, vol. 52, 1993, pp. 46-59.
Ugozzolli, L. et al., "Detection of Specific Alleles by Using Allele-Specific Primer Extension Followed by Capture on Solid Support," Genetic Analysis, Techniques and Applications, vol. 9, No. 4, 1992, pp. 107-112.
Wagle, Nikhil et al., "Dissecting Therapeutic Resistance to RAF Inhibition in Melanoma by Tumor Genomic Profiling," Journal of Clinical Oncology, vol. 29, No. 22, Aug. 2011, pp. 3085-3096.
Warbrick, E. et al., "The wis1 protein kinase is a dosage-dependent regulator of mitosis in *Schizosaccharomyces pombe*," The EMBO Journal, vol. 10, No. 13, 1991, pp. 4291-4299.
Wong, T-K. et al., "Appearance of β-lactamase activity in animal cells upon liposome-mediated gene transfer," Gene, vol. 10, 1980, pp. 87-94.
Zhang, Nan et al., "MEK (MAPKK) Inhibitors. Part 2: Structure-Activity Relationships of 4-Anilino-3-cyano-6,7-dialkoxyquinolines," Bioorganic & Medicinal Chemistry Letters, vol. 11, 2001, pp. 1407-1410.
International Search Report for International Application No. PCT/US2011/039789 dated Sep. 21, 2011; 4 pages.

\* cited by examiner

Wild-type Human MEK1 Nucleic Acid Sequence (SEQ ID NO:1) (NM_002755; gi:169790828)

AGGCGAGGCTTCCCCTTCCCCGCCCCTCCCCGGCCTCCAGTCCTCCCAGGGCCGCCTTCGCAGAGCGGCTAG
GAGCACGGCGGCGGGACTTTCCCCGGCACTTTGGTTGAGAGAGAGGAAGGAATCCCGGCTGGGCTGGCGCC
CCGAGCCGGAGGGACTGGTTGTGCAGGGCAGCCTTTGGCTCTCTGCGCGGCGGAATCCCGGCTGCCGAACCGCACGTTCAGC
CCGCTCCGCTCCTGCAGGGCAGCCTTTGGCTCTCTGCGCGGCGAGTCCCGGGCGGGGTGGGGCGGGGG
TCCACTGAGACCGCTACCGGCCCCTCGGCGCTGCGCAGCGGGGACCGCGCGGGGCGCACCCGCTGAAGGCAGCCCCG
GGGCCGCGCGGAGTTGGTCCTGCGCAGCGGGGGCGCGGGGAGCGCAGCGGCGGGAAGCGAGAGGTGCTG
CCCTCCCCGGAGTTGGAAGCGCGTTACCCGGGTCCAAAATGCCCAAGAAAGCCGACGCCCATCCAGCTGA
ACCCGGCCCCGACGGCTCTGCAGTTAACGGGACGCAGCCAGCTCTGCGGAGACCAACTTGGAGGCCTTGCAGAAGAAG
CTGGAGGAGCTAGAGCTTGATGAGCAGCAGAGGAAAGCGCTGGGGGGCTGGGCAATGCGGTGTGTTCAAGGTCTC
AGAACTGAAGGATGACGACTTTGAGAAGATCAGTGAGCTAGGGCCCTCCTAATTCATCTGGAGATCAAACCCGAATCCAGAT
CCACAAGCCTTCTGGCCTGGTCTGCATGAGCACATGGAGGTTCTCTGGATCAAGTCCTGAAGAAAGCTGGAAGAAT
CATAAGGGAGCTGCAGTTCTCGCATGAGTGCAACATGGAGGTTCTCTGGATCAAGTCCTGAAGAAAGCTGGAAGAAT
TGGCGAGATCAGTATCTGCAGGGTCTGCATGAGTGCAACATGGAGGTTCTCTGGATCAAGTCCTGAAGAAAGCTGGAAGAAT
TCCTGAACAAATTTAGGAAAAGTTAGCATTGCTGTAATAAAAGGCCTAGAAGCCTGGGGAGATCAAGCTCTGTGACTTTGGGTC
ATGCACAGAGATGTCAAGCCTCATCGACTCGATGTCCAACATCCTAGTCAACTCCGTGGGCACAAGGTCTCTCTGGTAGAGATGGCGGTTGGGAGGTAT
AGCGGGCAGCTCATTACTCTGTGCAGTCAGACATCTGGAGCATGGAGGACTGTCTCTGGTAGAGATGGCGGTTGGGAGGTAT
GGGACTCATTACTCTGTGCAGTCAGACATCTGGAGCATGGAGGACTGTCTCTGGTAGAGATGGCGGTTGGGAGGTAT
CCCATCCCTCCTCCAGATGCCAAGATCGTGCTGGAGCTGGAGCTGATGTTGGGGTGCCAGGTGGAAGGAGATGCGGCTGAGAC
CCACCCAGGCCAAGGACCCCGGAGGACCCCGGGAGGCCCCCTTAGCTCATACGGAATGACAGCCGACCTCCATGCAATT
TTGAGTGTGTTGGATTACATAGTCAAGCAGACCTCAACGAGCTCTCCAAAACTGCCCAGTGGAGTGTTCAGTCTGGAATTTCAAGA
TTTTGTGAATAAATGCTTAATAAAAAACCCCGCAGAGAGACAGATTTGAAGCAACTCATGGTTCATGCTTTTATCA
AGAGATCTGATGCTGAGGAAGTGGATTTTGCAGGTTGGCTCTGCTCCACCATCCGGCCTTAACCAGCCCAGCACAC
CAACCCATGCTGCTGGCGTCTAAGTGTTGGGAAGCAACAAAAGAGCGAGTCCCCTGCCCGGTGGTTTGCCATGTC
GCTTTTGGGCCTCCTTCCCATGCCTTGTCTCTGTCTTGTTCAGATGTGCATTCACCTGTGACAAAGGATGAAGAACACAGC
ATGTGCCAAGATTCTACTCTTGTCATTTTAATATTACTGTCTTTATTCTTATTACTGTGCCAGGCTGAATTACAGTGAAATTTTG
TGGCTTTGTGCTTGGGCTATTTGTGTGTATGCGATGATCAAAAACCTGTGCCAGGCTGAATTACAGTGAAATTTTG
GTGAATGTGGGTAGTCATTCTTACAATTGCACTGCTGTTCCTGCATGACTGGCTGTCTGCCTGTATTTCGGG
ATTCTTTGACATTTGGTGGTACTTTATTCTTGCTGCTATGAAAATGAGCATCAGAGAGTGTACATCATGTTATTTTTATT
CAGGCAGTGCATGTGAAGCATGCTTGCTGCTATGAAAATGAGCATCAGAGAGTGTACATCATGTTATTTTTATT
ATTATTTGCTTTCATGTAGAACTCAGCAGTTGACATCCAAATCTGGTATTCTATATTTTATTTCAGTATACTGTGTGG
GCTTCACCAGTCTGTCTACTGTGGTGATCGTAGACTTCTGTTAAGTTTCTTAAATGGAATTATTTGAATGTCACAAATTGATCAA
GATACTAGTAGTGATGTCTCTTTAAGTTTGATTAATGTTTCTTAAATGGAATTATTTGAATGTCACAAATTGATCAA
GATATTAAAATGTCGGATTTATCTTTCCCATATCCAAGTACCAATGCTGTTGTAAACAACGTGTATAGTGCCTAAA
TTGTATGAAATCCTTTAACCATTTAACCTAGATGTTTAACAAATCTAATCTCTATTCTAATAAATATACTATGAA
ATAAAAAAAAAAAGGATGAAAGCTAAAAAAAAAAAAAAAAAA

FIG. 3

Wild-type Human MEK1 Polypeptide Sequence (SEQ ID NO:2) (NP_002746; gi:5579478)

MPKKKPTPIQLNPAPDGSAVNGTSSAETNLEALQKKLEELELDEQQRKRLEAFLTQKQKVGELKDDDFEKIS
ELGAGNGGVVFKVSHKPSGLVMARKLIHLEIKPAIRNQIIRELQVLHECNSPYIVGFYGAFYSDGEISICMEHM
DGGSLDQVLKKAGRIPEQILGKVSIAVIKGLTYLREKHKIMHRDVKPSNILVNSRGEIKLCDFGVSGQLIDSMA
NSFVGTRSYMSPERLQGTHYSVQSDIWSMGLSLVEMAVGRYPIPPPDAKELELMFGCQVEGDAAETPPRP
RTPGRPLSSYGMDSRPPMAIFELLDYIVNEPPPKLPSGVFSLEFQDFVNKCLIKNPAERADLKQLMVHAFIKR
SDAEEVDFAGWLCSTIGLNQPSTPTHAAGV

FIG. 4

MEK1 MUTATION CONFERRING RESISTANCE TO RAF AND MEK INHIBITORS

RELATED APPLICATIONS

This application is a continuation of U.S. application Ser. No. 13/701,889, abandoned, which has a 35 U.S.C. § 371(c) date of Feb. 13, 2013, which claims the benefit under 35 U.S.C. § 371 of International Application No. PCT/US2011/039789, filed Jun. 9, 2011, which claims the benefit of the filing date under 35 U.S.C. § 119(e) of Provisional U.S. Patent Application Ser. No. 61/352,959, filed Jun. 9, 2010, which are incorporated by reference in their entirety.

FEDERALLY SPONSORED RESEARCH OR DEVELOPMENT

This invention was made with government support under federal grant number K08 CA115927 awarded by National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Jan. 28, 2016, is named Sequence listing 14293-501_ST25.txt and is approximately 14 KB in size.

BACKGROUND OF THE INVENTION

The treatment of cancer is one of the greatest challenges in modern medicine. While chemotherapeutic agents are typically an effective means of treating or reducing the symptoms associated with cancer, in some cases, resistance to one or more chemotherapeutic agents manifests during treatment. As a result, a given chemotherapeutic agent can become ineffective in certain individuals. The molecular mechanisms responsible for the development of resistance in various types of cancer are poorly understood. Elucidation of the mechanisms that underlie resistance to specific agents is essential to discovering treatment approaches that effectively circumvent drug resistance.

In particular, one type of cancer for which additional treatment approaches are needed is malignant melanoma. Malignant melanoma is the sixth most common cancer diagnosis in the US, with 68,729 estimated new cases in 2009. Metastatic melanoma is associated with a very poor prognosis, with a median survival of 6 to 15 months. In melanoma, uncontrolled activity of the MAP kinase pathway is nearly ubiquitous and occurs most commonly through gain-of-function mutations involving codon 600 of the BRAF oncogene (BRAF V600E). More than 50% of metastatic melanoma harbors BRAF V600E mutations. Moreover, BRAF V600E mutations have been found in 10% of colorectal cancers and in 8% of all solid tumors.

Recently, efforts to specifically target mutated BRAF in melanoma have yielded promising results. PLX4032 is an oral targeted drug that specifically inhibits BRAF V600E. In the Phase 1 trial of melanoma patients with BRAF V600E mutations, 70% of patients (19 of 27) had at least 30% tumor response by RECIST criteria. Phase II and Phase III trials of PLX4032 are currently underway. However, as with all other targeted therapies, resistance to PLX4032 has begun to emerge, with patients relapsing after an average of 9 months.

SUMMARY OF THE INVENTION

The present invention pertains to mutation-mediated resistance to chemotherapeutic treatment of cancer. In specific embodiments, the present invention is directed to a mutation identified in a MEK1 protein, and in nucleic acid molecules encoding the MEK1 protein, wherein the mutation comprises a substitution at amino acid position 121 of the wild-type MEK1 protein set forth in SEQ ID NO: 2. The mutation confers resistance to RAF and MEK inhibitors currently in therapeutic use. The identification of the mutation allows for the identification of cancer patients that may be susceptible to resistance to chemotherapeutic agents. Moreover, the identification of the mutation allows for the development of second-generation MEK inhibitors that exhibit activity against a MEK1 protein containing the resistance mutation, such as the mutation described herein. Such second-generation MEK inhibitors are useful in many clinical and therapeutic applications, including the treatment of cancer.

Accordingly, the invention features, in a first aspect, an isolated nucleic acid molecule encoding a mutant MEK1 protein having MEK1 activity, wherein said mutant MEK1 protein comprises an amino acid substitution at position 121 of wild-type MEK1 shown in SEQ ID NO: 2, the amino acid substitution conferring resistance to one or more RAF or MEK inhibitors on a cell expressing the mutant MEK1 protein. In various embodiments, the RAF inhibitor is selected from the group consisting of PLX4720, PLX4032, BAY 43-9006 (Sorafenib), ZM 336372, RAF 265, AAL-881, LBT-613, and CJS352. Preferred RAF inhibitors are the BRAF inhibitors PLX4720 and PLX4032. In various embodiments, the MEK inhibitor is selected from the group consisting of CI-1040, AZD6244, PD318088, PD98059, PD334581, RDEA119, Compound A, and Compound B. In some embodiments, the MEK inhibitor is the MEK1 inhibitor AZD6244. In some embodiments, the amino acid substitution is a 121C>S amino acid substitution. In some embodiments, the mutant MEK1 protein comprises the amino acid sequence of SEQ ID NO: 4. In some embodiments, the nucleic acid comprises nucleotide sequence of SEQ ID NO: 3.

The isolated nucleic acid molecules encoding mutant MEK1 proteins can be inserted into an expression vector and expressed in a host cell. Accordingly, in another aspect, the invention features an expression vector comprising a nucleic acid molecule as set forth herein. In another aspect, the invention features a host cell comprising the foregoing expression vector. In another aspect, the invention features a method of producing a mutant MEK1 protein, comprising culturing a host cell containing an expression vector encoding a mutant MEK1 protein, such that a mutant MEK protein is produced by the cell.

In other aspects, the invention features an isolated mutant MEK1 protein having MEK1 activity, wherein said mutant MEK1 protein comprises an amino acid substitution at position 121 of wild-type MEK1 protein shown in SEQ ID NO: 2, the amino acid substitution conferring resistance to one or more RAF or MEK inhibitors on a cell expressing the mutant MEK1 protein. In various embodiments, the RAF inhibitor is selected from the group consisting of PLX4720, PLX4032, BAY 43-9006 (Sorafenib), ZM 336372, RAF 265, AAL-881, LBT-613, and CJS352. In some embodiments, the RAF inhibitors are the BRAF inhibitors PLX4720 and PLX4032. In various embodiments, the MEK inhibitor is selected from the group consisting of CI-1040, AZD6244, PD318088, PD98059, PD334581, RDEA119, Compound A, and Compound B. In some embodiments, the MEK inhibitor is the MEK1 inhibitor AZD6244. In some embodiments, the amino acid substitution is a 121C>S amino acid substitution. In some embodiments, the mutant MEK1 protein comprises the amino acid sequence of SEQ ID NO: 4.

In another aspect, the invention features a method of identifying a compound that is useful in treating cancer, comprising: providing an assay composition comprising a mutant MEK1 protein, wherein the mutant MEK1 protein comprises an amino acid substitution at position 121 of wild-type MEK1 protein shown in SEQ ID NO: 2, and a MEK1 substrate; contacting the assay composition with a test compound under conditions that permit phosphorylation of the MEK1 substrate in the absence of the test compound; and determining the effect of the compound on phosphorylation of the MEK1 substrate; wherein downmodulation of phosphorylation of the MEK1 substrate as compared to a suitable control identifies the compound as a compound that is useful in treating cancer. In some embodiments, the mutant MEK1 protein comprises a 121C>S amino acid substitution.

In a related aspect, the invention features a method of identifying a compound as a second generation MEK1 inhibitor, comprising: providing an assay composition comprising a mutant MEK1 protein, wherein the mutant MEK1 protein comprises an amino acid substitution at position 121 of wild-type MEK1 protein shown in SEQ ID NO: 2, and a MEK1 substrate; contacting the assay composition with a test compound under conditions that permit phosphorylation of the MEK1 substrate in the absence of the test compound; and determining the effect of the compound on phosphorylation of the MEK1 substrate; wherein downmodulation of phosphorylation of the MEK1 substrate as compared to a suitable control identifies the compound as a second generation MEK1 inhibitor. In some embodiments, the mutant MEK1 protein comprises a 121C>S amino acid substitution.

In exemplary embodiments of the foregoing aspects, the MEK1 substrate is ERK1/2. In other embodiments, the assay composition is a cell extract.

In another aspect, the invention features a method of identifying a compound that is useful in treating cancer, comprising: providing a cell comprising a mutant MEK1 protein, wherein the mutant MEK1 protein comprises an amino acid substitution at position 121 of wild-type MEK1 protein shown in SEQ ID NO: 2; contacting the cell with a test compound; and determining the effect of the compound on ERK1/2 phosphorylation; wherein downmodulation of ERK1/2 phosphorylation as compared to an appropriate control identifies the compound as a compound that is useful in treating cancer. In a related aspect, the invention provides a method of identifying a compound that is a second generation MEK1 inhibitor, comprising: providing a cell comprising a mutant MEK1 protein, wherein the mutant MEK1 protein comprises an amino acid substitution at position 121 of wild-type MEK1 protein shown in SEQ ID NO: 2; contacting the cell with a test compound; and determining the effect of the compound on ERK1/2 phosphorylation; wherein downmodulation of ERK1/2 phosphorylation as compared to an appropriate control identifies the compound as a second generation MEK1 inhibitor. For some embodiments of both of these methods, the mutant MEK1 protein comprises a 121C>S amino acid substitution.

In another aspect, the invention features a method of identifying a compound that is useful in treating cancer, comprising: providing a cell comprising a mutant MEK1 protein, wherein the mutant MEK1 protein comprises an amino acid substitution at position 121 of wild-type MEK1 protein shown in SEQ ID NO: 2; contacting the cell with a test compound; and determining the effect of the compound on cell proliferation; wherein reduction in cell proliferation as compared to an appropriate control identifies the compound as a compound that is useful in treating cancer. In a related aspect, the invention provides a method of identifying a compound that is a second generation MEK1 inhibitor, comprising: providing a cell comprising a mutant MEK1 protein, wherein the mutant MEK1 protein comprises an amino acid substitution at position 121 of wild-type MEK1 protein shown in SEQ ID NO: 2; contacting the cell with a test compound; and determining the effect of the compound on cell proliferation; wherein reduction in cell proliferation as compared to an appropriate control identifies the compound as a second generation MEK1 inhibitor. For some embodiments of both of these methods, the mutant MEK1 protein comprises a 121C>S amino acid substitution.

In another aspect, the invention features a cell-based screening method for identifying a test compound as a second generation MEK1 inhibitor, the method comprising contacting a host cell with a test compound, wherein the host cell comprises a mutant MEK1 protein, wherein the mutant MEK1 protein comprises an amino acid substitution at position 121 of wild-type MEK1 protein shown in SEQ ID NO: 2, wherein sensitivity of the host cell to the test compound identifies the compound as a second-generation MEK1 inhibitor. In one embodiment of this aspect, sensitivity of the host cell to the test compound is measured using an assay selected from the group consisting of a cell proliferation assay, a cell viability assay, and a ERK1/2 phosphorylation assay, wherein a reduction in cell proliferation, cell viability, or ERK1/2 phosphorylation in the presence of the test compound identifies the compound as a second-generation MEK1 inhibitor. In some embodiments, the mutant MEK1 protein comprises a 121C>S amino acid substitution.

In another aspect, the invention features a method of identifying a second-generation MEK1 inhibitor, comprising: selecting a potential drug using computer-assisted modeling with a three-dimensional crystal or solution structure of a mutant MEK1 protein, wherein said mutant MEK1 protein comprises an amino acid substitution at position 121 of wild-type MEK1 protein shown in SEQ ID NO: 2; contacting said potential drug with the mutant MEK1 protein; and detecting the interaction of said potential drug with the mutant MEK1 protein; wherein a compound that is capable of interacting with the mutant MEK1 protein is identified as a second-generation MEK1 inhibitor. In some embodiments, the mutant MEK1 protein comprises a 121C>S amino acid substitution.

In one embodiment of the foregoing aspects, the test compound is a member of a library of compounds.

In another aspect, the invention features a compound identified by one of the foregoing methods. Such compounds are useful, for example, in inhibiting the activity of a mutant MEK1 protein comprising an amino acid substitution at position 121 of wild-type MEK1 protein shown in SEQ ID NO: 2, in some embodiments, a 121C>S amino acid substitution. Accordingly, in another aspect, the invention features a method of inhibiting the activity of a mutant MEK1 protein, wherein the mutant MEK1 protein comprises an amino acid substitution at position 121 of wildtype MEK1 protein shown in SEQ ID NO: 2 (preferably a 121C>S amino acid substitution), the method comprising contacting the mutant MEK1 protein with a compound identified according to one of the foregoing methods. In an exemplary embodiment, the compound inhibits the activity of a mutant MEK1 protein and a wild-type MEK1 protein. In one embodiment, said contacting occurs in vitro. In another embodiment, said contacting occurs in vivo. In another embodiment, said contacting occurs in a subject. In an exemplary embodiment, said contacting occurs in a subject having a cancer. In one embodiment, the subject having a cancer has relapsed from treatment with a RAF inhibitor, such as a RAF inhibitor selected from the group consisting of PLX4720, PLX4032, BAY 43-9006 (Sorafenib), ZM 336372, RAF 265, AAL-881, LBT-613, and CJS352 (preferably the BRAF inhibitors PLX4720 and PLX4032). Additionally or alternatively, the subject having cancer has relapsed from treatment with a first generation MEK inhibitor, such as a MEK inhibitor selected from the group consisting of CI-1040, AZD6244, PD318088, PD98059, PD334581, RDEA119, Compound A, and Compound B In some embodiments, the MEK1 inhibitor is AZD6244. In an exemplary embodiment, the cancer is a melanoma.

In another aspect, the invention features a method of treating a subject having a cancer, comprising administering to the subject a compound identified according to one of the foregoing methods. In an exemplary embodiment, the compound inhibits the activity of a mutant MEK1 protein, comprising an amino acid substitution at position 121 of wild-type MEK1 protein shown in SEQ ID NO: 2 (preferably a 121C>S amino acid substitution), and a wild-type MEK1 protein. In one embodiment, the subject having a cancer has relapsed from treatment with a RAF inhibitor, such as a RAF inhibitor selected from the group consisting of PLX4720, PLX4032, BAY 43-9006 (Sorafenib), ZM 336372, RAF 265, AAL-881, LBT-613, and CJS352. In some embodiments the BRAF inhibitors are selected from PLX4720 and PLX4032. Additionally or alternatively, the subject having cancer has relapsed from treatment with a first generation MEK inhibitor, such as a MEK inhibitor selected from the group consisting of CI-1040, AZD6244, PD318088, PD98059, PD334581, RDEA119, Compound A, and Compound B. In some embodiments, the MEK1 inhibitor is AZD6244. In a particular embodiment, the cancer comprises a MEK1 protein having a 121C>S amino acid substitution with respect to a wild type MEK1 protein, and/or a MEK1 nucleic acid molecule encoding a MEK1 protein having a 121C>S amino acid substitution with respect to a wild type MEK1 protein, wherein the 121C>S amino acid substitution confers resistance to one or more RAF or MEK inhibitors on cells expressing the mutant MEK1 protein. In an exemplary embodiment, the cancer is a melanoma.

In another aspect, the invention features a method of screening a subject having cancer, the method comprising obtaining a cancer cell-containing sample from the subject; and determining the presence or absence of an amino acid substitution at position 121 of wild type MEK1 protein, shown in SEQ ID NO: 2, in the cancer cell-containing sample. In some embodiments, the presence or absence of a 121C>S amino acid substitution is determined.

In one embodiment of the foregoing aspect, detection of the mutation at position 121 in the MEK1 protein identifies the subject as having a relatively high risk of relapse during treatment with a RAF inhibitor. In another embodiment, detection of the mutation at position 121 in the MEK protein identifies the subject as being unresponsive to treatment with a RAF inhibitor. In exemplary embodiments, the RAF inhibitor is selected from the group consisting of PLX4720, PLX4032, BAY 43-9006 (Sorafenib), ZM 336372, RAF 265, AAL-881, LBT-613, and CJS352. In some embodiments the BRAF inhibitor is selected from PLX4720 and PLX4032). In another embodiment of the foregoing aspect, the presence of the mutation at position 121 (preferably C121S) in the MEK1 protein stratifies the subject to treatment with a second generation MEK1 inhibitor that targets the mutant MEK1 protein. In another embodiment, the presence of the mutation at position 121 in the MEK1 protein stratifies the subject to treatment with a combination therapy that includes administration of both a RAF inhibitor and a second generation MEK1 inhibitor that targets the mutant MEK1 protein. In some embodiments, the mutation at position 121 is C121S.

In another aspect, the invention provides a method of identifying a subject having cancer as having a high risk of relapse during treatment with a RAF inhibitor, comprising:
(a) extracting nucleic acid from cells of the cancer; and
(b) sequencing a nucleic acid molecule encoding a MEK1 protein;
wherein the presence of nucleotides that produce a 121C>S amino acid substitution in the MEK1 protein, as compared to wild-type MEK1 protein, identifies the subject as having a high risk of relapse during treatment with a RAF inhibitor.

In another aspect, the invention provides a method of identifying a subject having cancer as being unresponsive to treatment with a RAF inhibitor, comprising:
(a) extracting nucleic acid from cells of the cancer; and
(b) sequencing a nucleic acid molecule encoding a MEK1 protein;
wherein the presence of nucleotides that produce a 121C>S amino acid substitution in the MEK1 protein, as compared to wild-type MEK1 protein, identifies the subject as being unresponsive to treatment with a RAF inhibitor.

In another aspect, the invention provides a method of optimizing treatment of a subject having cancer, comprising:
(a) extracting nucleic acid from cells of the cancer; and
(b) sequencing a nucleic acid molecule encoding a MEK1 protein;
wherein the presence of nucleotides that produce a 121C>S amino acid substitution in the MEK1 protein, as compared to wild-type MEK1 protein, indicates a need to treat the subject with a RAF inhibitor and a MEK inhibitor that targets a mutant MEK1 protein having a 121C>S amino acid substitution.

In another aspect, the invention provides a method of treating a subject having cancer, comprising:
(a) extracting nucleic acid from cells of the cancer;
(b) sequencing a nucleic acid molecule encoding a MEK1 protein; and
(c) administering a RAF inhibitor and a MEK inhibitor that targets a mutant MEK1 protein having a 121C>S amino acid substitution to the subject when the nucleic acid molecule contains nucleotides that produce a 121C>S amino acid substitution in the MEK1 protein, as compared to wild-type MEK1 protein.

In another aspect, the invention provides a method of treating a subject having cancer, comprising:
(a) extracting nucleic acid from cells of the cancer;
(b) subjecting the sample to PCR and identifying the nucleotide sequence of a nucleic acid molecule encoding a MEK1 protein;
(c) administering a RAF inhibitor and a MEK inhibitor that targets a mutant MEK1 protein having a 121C>S amino acid substitution to the subject when the nucleic acid molecule contains nucleotides that produce a 121C>S amino acid substitution in the MEK1 protein, as compared to wild-type MEK1 protein.

In another aspect, the invention provides a method of identifying a subject having cancer who is likely to benefit from treatment with a RAF inhibitor and a MEK inhibitor that targets a mutant MEK1 protein having a 121C>S amino acid substitution, comprising:
  (a) assaying a nucleic acid sample obtained from the cancer for the presence one or more mutations in a nucleic acid molecule encoding a MEK1 protein that produce a 121C>S amino acid substitution in the MEK1 protein, as compared to wild-type MEK1 protein; and
  (b) correlating the presence of the one or more mutations in a nucleic acid molecule encoding a MEK1 protein that produce a 121C>S amino acid substitution in the MEK1 protein with a subject who is likely to benefit from treatment with a RAF inhibitor and a MEK inhibitor that targets a mutant MEK1 protein having a 121C>S amino acid substitution.

In another aspect, the invention provides a method of identifying a subject having cancer who is likely to benefit from treatment with a MEK inhibitor that targets a mutant MEK1 protein having a 121C>S amino acid substitution, comprising:
  (a) extracting nucleic acid from cells of the cancer; and
  (b) sequencing a nucleic acid molecule encoding a MEK1 protein;
wherein the presence of nucleotides that produce a 121C>S amino acid substitution in the MEK1 protein, as compared to wild-type MEK1 protein, identifies the subject as being likely to benefit from treatment with a MEK inhibitor that targets a mutant MEK1 protein having a 121C>S amino acid substitution.

In various embodiments of the foregoing aspects, the RAF inhibitor is selected from the group consisting of PLX4720, PLX4032, BAY 43-9006 (Sorafenib), ZM 336372, RAF 265, AAL-881, LBT-613, and CJS35. In some embodiments, the RAF inhibitor is PLX4720 or PLX4032. In some embodiments of the foregoing aspects, the cancer is a leukemia, a lymphoma, a myeloma, a carcinoma, a metastatic carcinoma, a sarcoma, an adenoma, a nervous system cancer or a geritourinary cancer. In an exemplary embodiment, the cancer is a melanoma.

In another aspect, the invention provides kits for identifying a subject having cancer who has a high risk of relapse during treatment with a RAF inhibitor, or for identifying a subject having cancer who is unresponsive to treatment with a RAF inhibitor, or for optimizing treatment of a subject having cancer, or for identifying a subject having cancer who is likely to benefit from treatment with a RAF inhibitor and a MEK inhibitor that targets a mutant MEK1 protein having a 121C>S amino acid substitution, or for identifying a subject having cancer who is likely to benefit from treatment with a MEK inhibitor that targets a mutant MEK1 protein having a 121C>S amino acid, the kits comprising:
(a) a detection reagent useful for identifying the presence or absence of a mutation at amino acid position 121 in a MEK1 protein of SEQ ID NO:1 or SEQ ID NO:2; and (b) instructions describing a method set forth herein. In an exemplary embodiment, the detection reagent comprises nucleic acid primers useful for amplification of a MEK1 protein of SEQ ID NOs: 1 or 2.

In various embodiments of the foregoing aspects, the presence of a mutation at amino acid position 121 (e.g., a C121S mutation) in a MEK1 protein e.g., a MEK1 protein in a cancer cell-containing sample, is determined by a method comprising determining the sequence of a nucleic acid molecule encoding the MEK1 protein. In other embodiments, the presence of a mutation at amino acid position 121 in a MEK1 protein is determined using an antibody that recognizes a MEK1 protein comprising the mutation. In another embodiment, the foregoing methods further comprise administering a compound of identified according to a method described herein to a subject in whom the presence of one or more mutations in a MEK1 protein was detected.

In another aspect, the invention features a method of inhibiting a mutant MEK1 protein in a subject, the mutant MEK1 protein comprising an amino acid substitution at position 21 of wild-type MEK1 protein shown in SEQ ID NO: 2, the method comprising administering a compound identified by one of the foregoing methods to a subject in whom the presence of the mutant MEK1 protein was detected. In some embodiments the amino acid substitution is a 121C>S amino acid substitution.

BRIEF DESCRIPTION OF THE DRAWINGS

FIG. 2A is a photograph of an immunoblot. FIG. 2B is a bar graph quantitating the relative percent of phosphorylated ERK (pERK).

FIG. 3 depicts the wild-type human MEK1 nucleic acid sequence (SEQ ID NO:1) (Accession No. NM_002755; gi:169790828).

FIG. 4 depicts the wild-type human MEK1 protein sequence (SEQ ID NO:2) (Accession No. NP_002746; gi:5579478).

DETAILED DESCRIPTION OF THE INVENTION

Figures 1A, 1B:
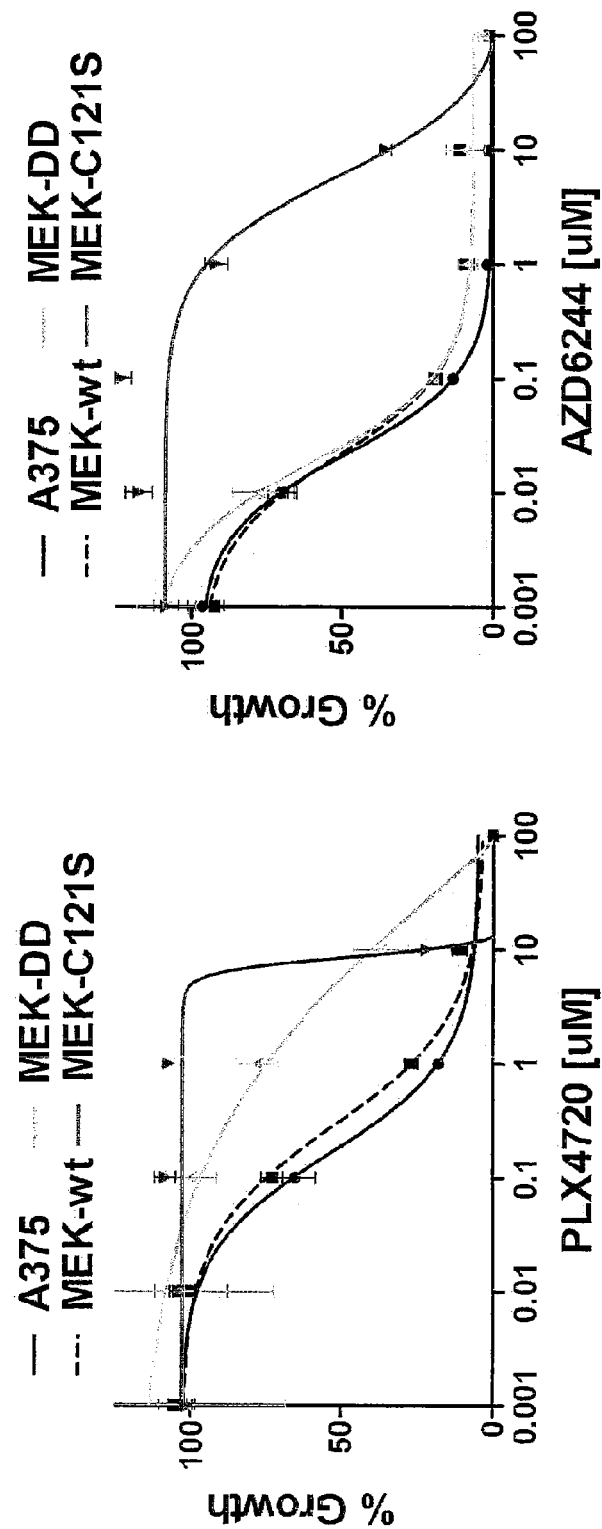
FIGS. 1A and 1B are graphs showing the percent growth inhibition of A375 melanoma cells treated with increasing concentrations (in μM) of either the BRAF inhibitor PLX4720 (FIG. 1A) or the MEK1 inhibitor AZD6244 (FIG. 1B), wherein the A375 cells were either untransfected (A375), transfected with wild-type MEK1 (MEK-WT), transfected with the MEK1 C121S mutant (MEK-C121S) or transfected with a constitutively active MEK variant (MEK-DD).

The present invention relates to the development of resistance to chemotherapeutic therapy for cancer, particularly resistance in malignant melanoma treated with a RAF inhibitor. Described herein is a patient with metastatic melanoma who developed resistance to the BRAF inhibitor PLX4032 after an initial dramatic response. As described in Example 1, massively parallel sequencing was used to conduct a comparative genomic analysis of 3 different DNA samples from the patient: (i) tumor that was sensitive to PLX4032, (ii) tumor that was resistant to PLX4032, and (iii) normal skin. A MEK1 mutation at amino acid position 121, in particular a C121S mutation, was identified as conferring resistance to the RAF inhibitor, as well as resistance to a MEK inhibitor, on cells expressing the mutant MEK1 protein. Thus, the development of a MEK1 mutation in response to BRAF-inhibition represents the first reported example in a patient of an acquired resistance mechanism in which the tumor develops an activating mutation downstream of the target kinase.

In an exemplary embodiment, the mutation at amino acid position 121 in the MEK1 protein confers resistance to the RAF inhibitors PLX4032 and PLX4720, as well as to the MEK inhibitor AZD6244. Accordingly, a "resistance mutation," as used herein, is a mutation in a MEK1 protein which confers resistance to one or more RAF or MEK inhibitors. As used herein, the term "resistance to one or more RAF or MEK inhibitors" is intended to mean that the resistance can be to one or more RAF inhibitors, one or more MEK inhibitors, or a combination of RAF and MEK inhibitors (e.g., a RAF inhibitor and a MEK inhibitor).

The identification of the mutation at amino acid position 121 in the MEK1 protein that confers resistance to RAF inhibitors, as well as MEK inhibitors, allows the development of "second-generation MEK inhibitors" the specifically target this mutant MEK1 protein. As used herein, the term "second-generation MEK inhibitor" refers to an agent that inhibits a biological activity of a MEK1 protein containing a mutation at amino acid position 121, such as the mutation described herein (C121S). In a preferred embodiment, a second-generation MEK inhibitor also inhibits a biological activity of a wild-type MEK1 protein. Accordingly, a second generation MEK inhibitor of the invention can inhibit a biological activity of a MEK1 protein containing a resistance mutation and can inhibit a biological activity of a wild-type MEK protein. Such second-generation MEK inhibitors are useful in many clinical and therapeutic applications, for example, in the treatment of cancer. In contrast, the term "first-generation MEK inhibitor," as used herein, refers to an agent that inhibits a biological activity of a wild-type MEK protein, but does not inhibit a biological activity of a MEK1 protein containing a resistance mutation at amino acid position 121, such as the mutation described herein.

Non-limiting examples of RAF inhibitors include PLX4720, PLX4032, BAY 43-9006 (Sorafenib), ZM 336372, RAF 265, AAL-881 (Novartis), LBT-613 (Novartis), and CJS352. PLX4720, PLX4032, BAY 43-9006 (Sorafenib), ZM 336372, RAF 265 are shown in Table 1. Additional RAF inhibitors known in the art may also be used.

TABLE 1

Exemplary RAF Inhibitors

| | Name | CAS No. | Structure |
|---|---|---|---|
| 1 | PLX4720 | 918505-84-7 | 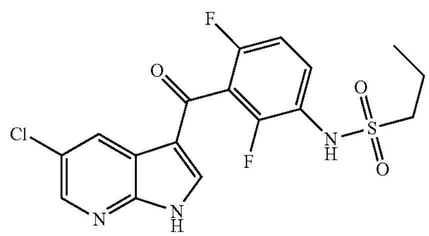 [SMILES: CCCS(=O)(=O)Nc1ccc(F)c(C(=O)c2c[nH]c3ncc(Cl)cc23)c1F] |
| 2 | PLX4032 | 1029872-54-5 | 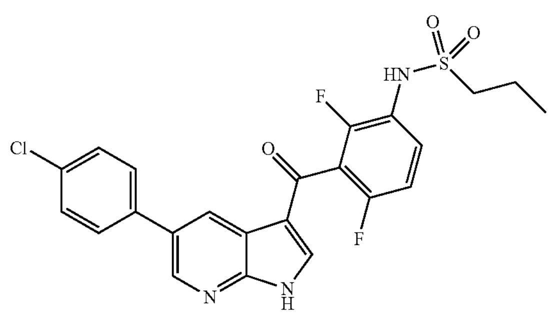 [SMILES: CCCS(=O)(=O)Nc1ccc(F)c(C(=O)c2c[nH]c3ncc(-c4ccc(Cl)cc4)cc23)c1F] |
| 3 | Bay 43-9006 Sorafenib Tosylate Nexavar | 475207-59-1 | $C_7H_8O_3S$ |

TABLE 1-continued

Exemplary RAF Inhibitors

| Name | CAS No. | Structure |
|---|---|---|
| 4 ZM 336372 | 208260-29-1 | (structure) |
| 5 RAF265 | 927880-90- | (structure) |

Non-limiting examples of MEK inhibitors include CI-1040, AZD6244, PD318088, PD98059, PD334581, RDEA119, Compound A, and Compound B (Table 2). Compounds A and B (6-Methoxy-7-(3-morpholin-4-yl-propoxy)-4-(4-phenoxy-phenylamino)-quinoline-3-carbonitrile and 4-[3-Chloro-4-(1-methyl-1H-imidazol-2-ylsulfanyl)-phenylamino]-6-methoxy-7-(3-morpholin-4-yl-propoxy)-quinoline-3-carbonitrile, respectively) are further described in Zhang et al., Bioorganic & Medicinal Chemistry Letters, 11(11):1407-1410 (2001) and Mallon et al., Mol Cancer Ther. June; 3(6):755-62 (2004), the entire contents of which are incorporated herein by reference.

TABLE 2

Exemplary MEK Inhibitors

| Name | CAS No. | Structure |
|---|---|---|
| 1 CI-1040/PD184352 | 212631-79-3 | (structure) |
| 2 AZD6244 | 606143-52-6 | (structure) |

TABLE 2-continued

Exemplary MEK Inhibitors

| | Name | CAS No. | Structure |
|---|---|---|---|
| 3 | PD318088 | 391210-00-7 | |
| 4 | PD98059 | 167869-21-8 | |
| 5 | PD334581 | | |
| 6 | RDEA119<br>N-[3,4-difluoro-2-[(2-fluoro-4-iodophenyl)amino]-6-methoxyphenyl]-1-[(2R)-2,3-dihydroxypropyl]-Cyclopropanesulfonamide | 923032-38-6 | |
| 7 | 6-Methoxy-7-(3-morpholin-4-yl-propoxy)-4-(4-phenoxy-phenylamino)-quinoline-3-carbonitrile | | |

TABLE 2-continued

Exemplary MEK Inhibitors

| Name | CAS No. | Structure |
| --- | --- | --- |
| 8 4-[3-Chloro-4-(1-methyl-1H-imidazol-2-ylsulfanyl)-phenylamino]-6-methoxy-7-(3-morpholin-4-yl-propoxy)-quinoline-3-carbonitrile | | |

The MEK inhibitors shown in Table 2 as well as additional MEK inhibitors known in the art may be tested using the methods described herein to determine if they are "first-generation MEK inhibitors" or "second-generation MEK inhibitors."

Identification of resistance mutations in the MEK1 protein also allows for the screening of patients having a cancer in order to determine the presence or absence of a MEK1 resistance mutation at amino acid position 121 in the cancer. Determining the presence or absence of one or more MEK resistance mutations in a cancer allows for alteration of the treatment strategy of a cancer patient. Such alterations can include, for example, starting or stopping treatment with a first generation MEK1 inhibitor or a RAF inhibitor, or starting or stopping treatment with a second generation MEK1 inhibitor.

Various aspects of the invention are described in further detail in the following subsections. Unless otherwise defined, all technical and scientific terms used herein have the same meaning as is commonly understood by one of ordinary skill in the art to which this invention belongs. In case of conflict, the present specification, including definitions, will control. Although methods and materials similar or equivalent to those described herein can be used in the practice of the invention, examples of suitable methods and materials are described below. The materials, methods, and examples described herein are illustrative only and are not intended to be limiting. All publications, patent applications, patents, and other references mentioned herein are incorporated by reference in their entirety.

I. MEK Biological Activity

As used herein, the terms "MEK1 protein" refers to a protein, also known as MKK1 (MAP kinase kinase 1), which is a dual-specific tyrosine and serine/threonine kinase that plays a key role in mitogen-activated protein kinase (MAPK) intracellular signaling. MEK1 is approximately 45 kDa in size, and is expressed ubiquitously in mammalian cells. MEK1 contains an activation loop that includes two serine residues at positions 217 and 221. Phosphorylation of these residues by the protein kinase Raf results in MEK1 activation during MAPK signaling. MEK1 also contains two regulatory phosphorylation sites outside the activation loop. Phosphorylation at Serine 298 may help prime MEK1 for activation. Conversely, phosphorylation at Serine 212 may decrease MEK1 activity.

The mitogen-activated protein kinase (MAPK) cascade is a critical intracellular signaling pathway that regulates signal transduction in response to diverse extracellular stimuli, including growth factors, cytokines, and proto-oncogenes. Activation of this pathway results in transcription factor activation and alterations in gene expression, which ultimately lead to changes in cellular functions including cell proliferation, cell cycle regulation, cell survival, angiogenesis and cell migration. Classical MAPK signaling is initiated by receptor tyrosine kinases at the cell surface, however many other cell surface molecules are capable of activating the MAPK cascade, including integrins, heterotrimeric G-proteins, and cytokine receptors.

Ligand binding to a cell surface receptor, e.g., a receptor tyrosine kinase, typically results in phosphorylation of the receptor. The adaptor protein Grb2 associates with the phosphorylated intracellular domain of the activated receptor, and this association recruits guanine nucleotide exchange factors including SOS-1 and CDC25 to the cell membrane. These guanine nucleotide exchange factors interact with and activate the GTPase Ras. Common Ras isoforms include K-Ras, N-Ras, H-Ras and others. Following Ras activation, the serine/threonine kinase Raf (e.g., A-Raf, B-Raf or Raf-1) is recruited to the cell membrane through interaction with Ras. Raf is then phosphorylated. Raf directly activates MEK1 and MEK2 by phosphorylation of two serine residues at positions 217 and 221. Following activation, MEK1 and MEK2 phosphorylate tyrosine (Tyr-185) and threonine (Thr-183) residues in serine/threonine kinases Erk1 and Erk2, resulting in Erk activation. Activated Erk regulates many targets in the cytosol and also translocates to the nucleus, where it phosphorylates a number of transcription factors regulating gene expression. Erk kinase has numerous targets, including Elk-1, c-Ets1, c-Ets2, p90RSK1, MNK1, MNK2, MSK1, MSK2 and TOB. While the foregoing pathway is a classical representation of MAPK signaling, there is considerable cross talk between the MAPK pathway and other signaling cascades.

Aberrations in MAPK signaling have a significant role in cancer biology. Altered expression of Ras is common in many cancers, and activating mutations in Ras have also been identified. Such mutations are found in up to 30% of all cancers, and are especially common in pancreatic (90%) and colon (50%) carcinomas. In addition, activating Raf mutations have been identified in melanoma and ovarian cancer. The most common mutation, BRAF 600V>E, results in constitutive activation of the downstream MAP kinase pathway and is required for melanoma cell proliferation, soft agar growth, and tumor xenograft formation. Based on the defined role of MAPK over-activation in human cancers, targeting components of the MAPK pathway with specific inhibitors is a promising approach to cancer therapy. MEK1 and MEK2 are attractive targets for therapy because of the high degree of specificity they display for their Erk1/2 substrates. The high degree of homology between MEK1 and MEK2 make it likely that a small-molecule MEK inhibitor would effectively inhibit both proteins. CI-1040 (also known as PD184352) is a MEK inhibitor that has been tested in Phase I and Phase II clinical trials. CI-1040 was found to inhibit MEK1 with an in vitro $IC_{50}$ of 17 nmol/L (Friday et al. Clin. Cancer Res. (2008) 14(2):342-346; incorporated herein by reference in its entirety). CI-1040 additionally inhibited MEK in cell-based assays, and reduced human colon cancer xenograft growth, indicating that MEK inhibition is a viable method of cancer therapy.

As used interchangeably herein, the terms "MEK1 activity," "MEK1 biological activity" or "functional activity of MEK1," include activities exerted by a MEK1 protein on a MEK responsive cell or tissue, e.g., a cancer cell, or on a MEK nucleic acid molecule or protein target molecule, as determined in vivo or in vitro, according to standard techniques. MEK1 activity can be a direct activity, such as an association with a MEK-target molecule e.g., ERK1/2, or phosphorylation of a substrate (e.g., ERK1/2). Alternatively, a MEK1 activity is an indirect activity, such as a downstream biological event mediated by interaction of the MEK1 protein with an MEK target molecule, e.g., ERK1/2. As MEK is in a signal transduction pathway involving ERK1/2, modulation of MEK1 modulates a molecule in a signal transduction pathway involving ERK1/2.

II. MEK Resistance Mutations

While treatment of cancer with RAF inhibitors, such as PLX4032, or with MEK inhibitors, including AZD6244 and CI-1040, are promising therapeutic approaches, patients receiving such therapies frequently relapse or fail to respond, and as a result the patients' disease progresses. As described herein, the present invention relates to the discovery of a mutation in MEK1 that confer resistance to RAF and MEK inhibitors currently in clinical development. Acquisition of such a mutation in cancer cells makes patients resistant to treatment with certain RAF and MEK inhibitors. In exemplary embodiments, the invention regards development of resistance to the RAF inhibitors PLX4032 and PLX4720 and the MEK inhibitor AZD6244.

The clinical emergence of a resistant MEK1 mutation in metastatic $BRAF^{V600E}$ melanoma as described herein suggests that the biological relevance of RAF/MEK-associated dependency is maintained even in advanced stages of malignancy. Thus, the failure of first-generation RAF or MEK inhibitors to elicit durable tumor responses in many $BRAF^{V600E}$ melanomas may indicate suboptimal drug potency or pharmacodynamics in the clinical setting. Based on the findings described herein, treatment modalities involving targeted agents in RAF- or MEK-driven tumors may benefit from more potent drugs, altered dosing of existing drugs, or combined RAF and MEK inhibition. These therapeutic innovations, together with robust tumor genomic profiling to stratify patients, should speed the advent of personalized cancer treatment in cancers with "druggable" oncogene mutations.

(A) Identification of MEK1 Mutation Conferring Resistance to RAF and MEK Inhibitors In various embodiments, the present invention relates to methods of identifying mutations in a MEK1 protein, or mutations in a nucleic acid molecule encoding the MEK1 protein, that confer resistance on cells expressing the MEK1 protein to drugs that inhibit RAF or MEK activity. A "mutant MEK1 protein," as referenced herein, includes a MEK1 protein containing one or more mutations that confer resistance to one or more known RAF or MEK inhibitors. Likewise, a "mutant MEK1 nucleic acid molecule," as referenced herein, includes a nucleic acid molecule that encodes a mutant MEK1 protein. Nucleic acid molecules encoding MEK1 proteins that contain one or more mutations can be created using any suitable method known in the art, including, for example, random mutagenesis or site-directed mutagenesis of a wild-type MEK1 nucleic acid sequence, which can be conducted in *E. coli*. In exemplary embodiments, the wild-type MEK1 nucleic acid sequence is a human wild-type MEK1 nucleic acid sequence. In specific embodiments the wild-type MEK1 nucleic acid sequence is wild-type human MEK1 (SEQ ID NO:1), shown in FIG. 3. The mutant MEK1 nucleic acid molecules can then be screened in cells otherwise sensitive to treatment with a RAF or MEK inhibitor to identify a nucleic acid that encodes a mutant MEK1 protein that is resistant to treatment with the RAF or MEK inhibitor.

Any suitable method can be used to screen mutant MEK1 nucleic acids and mutant MEK1 proteins for resistance to treatment with a RAF or MEK inhibitor. For example, a nucleic acid molecule encoding a mutant MEK1 protein can be expressed in cells otherwise sensitive to treatment with a RAF or MEK inhibitor. An exemplary cell line useful for this purpose is the melanoma cell line A375. Following expression of the mutant MEK1 protein, the cells can be treated with a RAF or MEK inhibitor. The activity of the mutant MEK1 protein can then be measured and compared to the activity of a wild-type MEK1 protein similarly expressed and treated with the RAF or MEK inhibitor. Activity of a MEK1 protein can be determined by, for example, measuring proliferation or viability of cells following treatment with the RAF or MEK inhibitor, wherein proliferation or viability are positively correlated with MEK1 activity. Cell growth, proliferation, or viability can be determined using any suitable method known in the art. In one embodiment, cell growth can be determined using well-based cell proliferation/viability assays such as MTS or Cell Titer GLo, in which cell growth in the presence of a RAF or MEK inhibitor is expressed as a percentage of that observed in untreated cells cultured in the absence of the RAF or MEK inhibitor. In certain embodiments, resistance is defined as a shift in the GI50 value of at least 2 fold, more preferably at least 3 fold, most preferably at least 4-5 fold, with respect to a suitable control. In other embodiments, resistance is defined as a GI50 value of ~1 uM). Activity of a MEK1 protein can also be measured by, for example, determining the relative amount of phosphorylated ERK1/2 present in the cell following treatment with the RAF or MEK inhibitor. Activity of a wild-type or mutant MEK1 protein can also be determined using an in vitro phosphorylation assay, in which MEK1 activity is determined by measuring the proportion of phosphorylated ERK 1/2 substrate in the assay following treatment with the RAF or MEK inhibitor. A mutant MEK1 protein having greater activity than a wild-type MEK1 protein following treatment with a RAF or MEK inhibitor is identified as containing a mutation that confers resistance to a RAF or MEK inhibitor. The mutation conferring resistance to a RAF or MEK inhibitor can then be identified by sequencing the nucleic acid encoding the mutant MEK1 protein, or by sequencing the mutant MEK1 protein directly.

In this manner, as well as using massively parallel sequence methods, as described in Example 1, an amino acid substitution at position 121 of the human MEK1 protein was identified that, when mutated, confers resistance to the RAF inhibitors PLX4032 and PLX4720, as well as the MEK inhibitor AZD6244. In particular, a substitution of the wild-type cysteine at position 121 with serine (referred to herein as C121S or 121C>S) was identified as conferring resistance to RAF and MEK inhibitors. Moreover, the invention encompasses other substitutions at amino acid position 121 of MEK1 that confer resistance to one or more RAF or MEK inhibitors. For example, substitutions of the cysteine at position 121 with other amino acid structurally similar to serine, such as alanine, threonine or glycine, are encompassed by the invention. Thus, in various embodiments, the mutant MEK1 protein of the invention can comprise a mutation such as C121A, C121T or C121G.

As described herein, identification of mutations in MEK conferring resistance to RAF or MEK inhibitors allows the design and screening of "second generation MEK inhibitors," which are effective at inhibiting a mutant MEK1 protein having a resistance mutation at amino acid position 121. Such second-generation MEK inhibitors are useful in many clinical and therapeutic applications, for example, in the treatment of cancer. Identification of resistance mutations in the MEK1 protein also allows the screening of patients having a cancer in order to determine the presence or absence of a MEK1 resistance mutations at position 121 in the cancer. Determining the presence or absence of a MEK1 resistance mutation at position 121 in a cancer allows alteration of the treatment strategy of a cancer patient. For example, identification of a MEK1 resistance mutation described herein in a cancer cell-containing sample from a patient having a cancer can be used to stratify the patient to treatment with a second-generation MEK1 inhibitor. Identification of MEK1 resistance mutations also allows the screening and identification of patients having a high risk of relapse or lack of response to treatment with certain RAF or MEK inhibitors.

The foregoing MEK1 resistance mutations also confer resistance to inhibitors of RAF kinase, e.g., the B-RAF inhibitor PLX4720. Resistance to inhibitors of a RAF kinase can be determined, for example, by measuring the activity a mutant MEK1 protein in the presence of a RAF inhibitor, and comparing the activity to that of a wild-type MEK1 protein similarly treated with the RAF inhibitor. Activity of a MEK1 protein can be determined using the methods set forth herein.

III. Methods for Identifying Second-Generation MEK Inhibitors

Identification of MEK1 resistance mutations allows the development and/or identification of "second-generation MEK1 inhibitors." As used herein, a second-generation MEK1 inhibitor is an agent that effectively inhibits the activity of a mutant MEK1 protein containing a mutation at amino acid position 121 as described herein. A second-generation MEK1 inhibitor may or may not inhibit the activity of a wild-type MEK1 protein in addition to a mutant MEK1 protein. In a preferred embodiment, a second-generation MEK1 inhibitor inhibits the activity of both a wild-type MEK1 protein and a mutant MEK1 protein. In an exemplary embodiment, a second-generation MEK1 inhibitor inhibits the activity of a MEK1 protein containing a mutation at amino acid position 121, preferably a C121S mutation.

Accordingly, the present invention provides methods for identifying a test compound as a second-generation MEK1 inhibitor. In one embodiment, a compound can be identified as a second-generation MEK1 inhibitor by determining the relative MEK1 activity of a mutant MEK1 protein (having a substitution at position 121) in the presence or absence of the compound, with respect to a wild-type MEK1 protein. When in the presence of a compound that is a second-generation MEK1 inhibitor, a mutant MEK1 protein has a lower level of MEK1 activity than in the absence of the compound. When in the presence of a compound that is not a second-generation MEK1 inhibitor, a mutant MEK1 protein has an equivalent or higher level of MEK1 activity than in the absence of the compound. In certain embodiments, MEK1 activity can be measured in an in vitro assay using recombinant MEK1 proteins. In other embodiments, MEK1 activity can be measured in an in vivo assay using cultured cells or experimental animals.

Any indicator of MEK1 activity is suitable for determining whether or not a compound is a second-generation MEK1 inhibitor. In an exemplary embodiment, MEK1 activity is determined by measuring phosphorylation of the MEK substrate ERK1/2, wherein a decrease in ERK1/2 phosphorylation indicates a decrease in MEK1 activity. In one embodiment, ERK1/2 phosphorylation is measured in a cell or cell extract. In an alternate embodiment, ERK1/2 phosphorylation is measured in an in vitro phosphorylation assay using purified or recombinant proteins. Methods of detecting ERK1/2 phosphorylation known in the art are suitable for measuring ERK1/2 phosphorylation as an indication of the activity of a MEK1 protein or a mutant MEK1 protein. Such methods include, but are not limited to, Western blot and mass spectroscopy. In certain embodiments, an ERK1/2 phosphorylation assay can be performed in vitro using recombinant proteins. In other embodiments, an ERK1/2 phosphorylation assay can be performed in vivo using cultured cells or experimental animals.

In one embodiment, a host cell expressing a mutant MEK1 protein is used in the identification of a second-generation MEK1 inhibitor, wherein the sensitivity of the host cell to a test compound identifies the test compound as a second-generation MEK1 inhibitor. As used herein, the term "sensitivity of the host cell to a test compound" is intended to mean that the test compound has a measurable effect on one or more parameters including cell growth, cell proliferation, cell viability and/or intracellular signal transduction (e.g., signal transduction mediated by MEK1 as evidenced by, for example, phosphorylation of one or more MEK substrates, such as ERK1/2).

A compound can be identified as a second-generation MEK1 inhibitor by determining the viability or proliferation rate of cells expressing a mutant MEK1 protein in the presence or absence of the compound. The cell line used in such an assay should be sensitive to a MEK1 inhibitor when the cell line expresses a wild-type MEK1 protein, and should be resistant to the MEK1 inhibitor (i.e., a first-generation MEK inhibitor) when the cell line expresses a mutant MEK1 protein. An exemplary cell line useful for identification of a second-generation MEK1 inhibitor is the melanoma cell line A375. A375 cells are sensitive to the MEK1 inhibitor AZD6244 when expressing a wild-type MEK1 protein, but are resistant to AZD6244 when expressing a mutant MEK1 protein, for example, a MEK1 protein comprising a C121S mutation.

When in the presence of a compound that is a second-generation MEK1 inhibitor, a cell line expressing a mutant MEK1 protein has a lower viability or proliferation rate than in the absence of the compound, and/or a lower viability or proliferation rate than a cell line expressing a wild type MEK1 protein in the presence of the compound. When in the presence of a compound that is not a second-generation MEK1 inhibitor, a cell line expressing a mutant MEK1 protein has an equivalent or higher viability or proliferation rate than in the absence of the compound, and/or an equivalent or higher viability or proliferation rate than a cell line expressing a wild type MEK1 protein in the presence of the compound. Methods of measuring cell viability and/or proliferation rate known in the art are suitable for determining the sensitivity of a cell line expressing a MEK1 protein or a mutant MEK1 protein to a test compound. Such methods include, but are not limited to, measurement of Trypan blue exclusion, metabolism of tetrazolium compounds, tritiated thymidine incorporation, BrdU incorporation, glucose uptake, ATP concentration, and level of apoptosis. In one embodiment, cell proliferation can be determined using well-based cell proliferation/viability assays such as MTS or Cell Titer GLo. In certain embodiments, sensitivity is defined as a shift in the GI50 value of at least 2 fold, more preferably at least 3 fold, most preferably at lease 4-5 fold, with respect to a suitable control.

Accordingly, in one embodiment, the invention provides a method of identifying a compound that is a second generation MEK1 inhibitor, comprising providing an assay composition comprising a MEK substrate and a MEK1 protein having a mutation at position 121 with respect to a wild-type MEK1 protein (e.g., a C121S mutation), contacting the assay composition with a test compound under conditions that permit phosphorylation of the MEK substrate in the absence of the test compound, and determining the effect of the compound of phosphorylation of the MEK substrate, wherein downmodulation of phosphorylation of the MEK substrate as compared to a suitable control identifies the compound as a second generation MEK1 inhibitor. A compound identified in this way is a compound useful for treating a cancer, e.g., a cancer in which a mutant MEK1 protein has been detected. A MEK1 protein useful in the foregoing methods is a MEK1 protein containing a mutation which confers resistance to one or more MEK, e.g., a MEK1 protein containing one or more of the mutations described herein. A MEK substrate useful in the foregoing methods is ERK1/2. A decrease, reduction, or downmodulation of ERK1/2 phosphorylation is an indication that the compound is a MEK1 inhibitor. The foregoing methods can be performed in vitro wherein the MEK1 protein and the MEK substrate are isolated or purified proteins. The foregoing methods can also be performed in vitro wherein the MEK1 protein and the MEK substrate are components of a cell extract. In this embodiment, the assay composition is a cell extract. A suitable control is any control that would be apparent to a skilled person performing the method, and includes, for example, a similar or identical assay composition not treated with a test compound or treated with a control compound, or an analogous assay composition or cell extract comprising a "wild-type" MEK1 protein.

In another embodiment, the invention provides a method of identifying a compound that is a second generation MEK1 inhibitor, comprising providing a cell comprising a mutant MEK1 protein comprising a mutation at position 121 (e.g., a C121S mutation), contacting the cell with a test compound, and determining the effect of the compound on ERK1/2 phosphorylation or cell proliferation, wherein a decrease, reduction, or downmodulation of ERK1/2 phosphorylation or cell proliferation as compared to an appropriate control identifies the compound as a second generation MEK1 inhibitor. A compound identified in this way is a compound useful for treating a cancer, e.g., a cancer in which a mutant MEK1 protein has been detected. A suitable control is any control that would be apparent to a skilled person performing the method, and includes, for example, a similar or identical cell not treated with a test compound or treated with a control compound, or an analogous cell or cell extract in which recombinant, "wild-type" MEK1 was expressed.

In one embodiment, the test compound used in the foregoing methods is a MEK inhibitor that inhibits a biological activity of a wild type MEK1 protein. MEK inhibitors that are second generation MEK1 inhibitors are described herein.

In another embodiment, the test compound is a member of a library of test compounds. A "library of test compounds" refers to a panel comprising a multiplicity of test compounds. An approach for the synthesis of molecular libraries of small organic molecules has been described (Carell et al. (1994). *Angew. Chem. Int. Ed. Engl.* 33:2059; Carell et al. (1994) *Angew. Chem. Int. Ed. Engl.* 33:2061). The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422; Horwell et al. (1996) *Immunopharmacology* 33:68-; and in Gallop et al. (1994); *J. Med. Chem.* 37:1233-. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249: 386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310). In still another embodiment, the combinatorial proteins are produced from a cDNA library. Exemplary compounds that can be screened for activity include, but are not limited to, peptides, nucleic acids, carbohydrates, small organic molecules, and natural product extract libraries.

Second generation MEK inhibitors can also be rationally designed based on the structure of MEK1 alleles containing a resistance mutation described herein. As described herein, a substitution at position 121 of MEK1 that confers resistance to RAF or MEK inhibitors is located in or near the C-helix of the MEK1 protein. Identification of MEK1 mutant alleles conferring resistance to RAF and MEK inhibitors allows comparison between the structure of the C-helix of the mutant alleles and the wild-type protein. Knowledge of the altered structural features that confer resistance to RAF and MEK inhibitors allows rational design and construction of ligands, including inhibitors, that will bind the C-helix, activation loop, and/or the ATP binding pocket of the mutant alleles. Such inhibitors can be designed such that they bind both the mutant and wild-type MEK1 alleles. Inhibitors designed to bind the C-helix, activation loop, and/or ATP binding pocket of MEK1 alleles containing mutations described herein are second-generation MEK1 inhibitors. The ability of such rationally designed inhibitors to inhibit a biological activity of a mutant MEK1 protein can be confirmed using the in vitro and/or in vivo assays described herein.

The structure of a MEK protein containing a resistance mutation described herein can be determined by computer-assisted modeling, or by determining the crystal or solution structure of the mutant MEK1 protein. Any suitable method known in the art can be used to determine the structure of a mutant MEK1 protein.

Exemplary computer-assisted modeling methods include the use of software programs such as PYMOL, CAVITY (described in J. Comp. Aided. Mol. Des. (1990) 4:337-354 (incorporated herein by reference)) and Discovery Studio® (Accelrys, San Diego, Calif.). Additional techniques useful for computer-assisted molecular modeling are described in J BUON. (2007) 12 Suppl 1:S101-18 (incorporated herein by reference). Computer-based analysis of a protein with a known structure can also be used to identify molecules which will bind to the protein. Such methods rank molecules based on their shape complementary to a receptor site. For example, using a 3-D database, a program such as DOCK can be used to identify molecules which will bind to XBP-1, IRE-1 alpha, and/or EDEM. See DesJarlias et al. (1988) J. Med. Chem. 31:722; Meng et al. (1992) J. Computer Chem. 13:505; Meng et al. (1993) Proteins 17:266; Shoichet et al. (1993) Science 259:1445. In addition, the electronic complementarity of a molecule to a targeted protein can also be analyzed to identify molecules which bind to the target. This can be determined using, for example, a molecular mechanics force field as described in Meng et al. (1992) J. Computer Chem. 13:505 and Meng et al. (1993) Proteins 17:266. Other programs which can be used include CLIX which uses a GRID force field in docking of putative ligands (see, for example, Lawrence et al. (1992) Proteins 12:31; Goodford et al. (1985) J. Med. Chem. 28:849; and Boobbyer et al. (1989) J. Med. Chem. 32:1083, incorporated by reference in their entirety).

Crystallization can be performed by any crystallization method including, but not limited to batch, dialysis and vapor diffusion (e.g., sitting drop and hanging drop) methods. Micro, macro and/or streak seeding of crystals can also be performed to facilitate crystallization. Crystals comprising MEK1 mutant alleles can be formed by a variety of different methods known in the art. For example, crystallizations can be performed by batch, dialysis, and vapor diffusion (sitting drop and hanging drop) methods. A detailed description of basic protein crystallization setups can be found in McRee, D., *Practical Protein Crystallography*, 2$^{nd}$ Ed. (1999), Academic Press Inc. Further descriptions regarding performing crystallization experiments are provided in Stevens et al. (2000) *Curr. Opin. Struct. Biol.:* 10(5):558-63, and U.S. Pat. Nos. 6,296,673; 5,419,278; and 5,096,676, the entire contents of which are incorporated herein by reference. Such crystals can be used to perform X-ray or neutron diffraction analysis in order to determine the three-dimensional structure of MEK1 mutant alleles. A solution structure of a MEK1 protein or mutant MEK1 protein can be identified using nuclear magnetic resonance spectroscopy using techniques known in the art. Suitable methods for protein structure determination by X-Ray crystallography or NMR spectroscopy are described in Brunger et al., (1998) "Crystallography & NMR system (CNS): A new software system for macromolecular structure determination," Acta Crystallogr D54, 905-921; Brunger et al. (1987) "Solution of a Protein Crystal Structure With a Model Obtained From NMR Interproton Distance Restraints," Science 235, 1049-1053; Drenth, "Principles of Protein X-ray Crystallography," (1994), Springer-Verlag. pp. 1-19; and Narula et al. (1995) "Solution structure of the C-terminal SH2 domain of the human tyrosine kinase Syk complexed with a phosphotyrosine pentapeptide," Structure 3, 1061-1073, incorporated herein by reference in their entirety. Upon identification of the crystal or solution structure of a mutant MEK1 protein, inhibitors of the mutant MEK1 protein can be identified using the computer assisted modeling approaches described above.

Second-generation MEK1 inhibitors identified by the foregoing methods are useful for treating a disease or condition associated with expression of a wild-type and/or mutant MEK1 protein. For example, second-generation MEK1 inhibitors are useful for treating a cancer in a subject, particularly a cancer in which a mutant MEK1 protein comprising a substitution at position 121 has been identified. In an exemplary embodiment, second-generation MEK1 inhibitors are useful for treating a cancer containing a MEK1 protein having a C121S mutation.

IV. Isolated Nucleic Acid Molecules

The present invention concerns polynucleotides or nucleic acid molecules relating to the MEK1 gene and its respective gene product. These polynucleotides or nucleic acid molecules are isolatable and purifiable from mammalian cells. In particular aspects of the invention, the isolated MEK1 nucleic acid molecules described herein comprise a mutation conferring resistance to one or more RAF or MEK inhibitors. A "mutant MEK1 nucleic acid molecule," as referenced herein, includes a MEK1 nucleic acid molecule that encodes a mutant MEK1 protein, i.e., a MEK protein containing one or more mutations that confer resistance to one or more known RAF or MEK inhibitors.

In a preferred embodiment, the isolated nucleic acid of the invention encoding a mutant MEK1 protein comprises the nucleotide sequence set forth in SEQ ID NO: 3. In yet another embodiment, the isolated nucleic acid of the invention encodes a mutant MEK1 protein comprising the amino acid sequence set forth in SEQ ID NO: 4.

It is contemplated that an isolated and purified MEK1 nucleic acid molecule, e.g., a mutant MEK1 nucleic acid molecule, can take the form of RNA or DNA. As used herein, the term "RNA transcript" refers to an RNA molecule that is the product of transcription from a DNA nucleic acid molecule. Such a transcript can encode for one or more proteins.

As used in this application, the term "polynucleotide" refers to a nucleic acid molecule, RNA or DNA, that has been isolated, such as being free of total genomic nucleic acid. Therefore, a "polynucleotide encoding MEK1" refers to a nucleic acid segment that contains MEK1 coding sequences, yet is isolated away from, or purified and free of, total genomic DNA and proteins. When the present application refers to the function or activity of a MEK1-encoding polynucleotide or nucleic acid, it is meant that the polynucleotide encodes a molecule that is capable of performing an activity of a wild-type MEK1 protein, for example, phosphorylation of the ERK1/2 substrate.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 1989; Ausubel, 1996). There can be times when the full or partial genomic sequence is preferred. Alternatively, cDNA can be advantageous because it represents coding regions of a protein and eliminates introns and other regulatory regions.

It also is contemplated that a given MEK1-encoding nucleic acid or MEK1 gene from a given cell may be represented by natural variants or strains that have slightly different nucleic acid sequences but, nonetheless, encode an active MEK1 protein. In a preferred embodiment, the active MEK1 protein is an active human MEK1 protein. In particularly preferred embodiments, the active MEK1 protein is a mutant MEK1 protein that has an activity of a wild-type MEK1 protein, but which is resistant to one or more known RAF or MEK inhibitors. Consequently, certain aspects of the present invention encompass derivatives of MEK1 with minimal amino acid changes, but that possess the same biological function.

The term "gene" is used for simplicity to refer to a functional protein, protein, or peptide-encoding unit. As will be understood by those in the art, this functional term includes genomic sequences, cDNA sequences, and smaller engineered gene segments that express, or can be adapted to express, proteins, proteins, domains, fusion proteins, and mutant proteins. The nucleic acid molecule encoding MEK1 can comprise a contiguous nucleic acid sequence of the following lengths: at least about 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences can be identical or complementary to, for example, SEQ ID NO:1, or a fragment thereof.

Various embodiments of the invention relate to genetic mutations in MEK1. As used herein, a mutation refers to an addition, deletion, or substitution of a single nucleotide at a site in a MEK1 nucleic acid molecule. In an exemplary embodiment, a mutant MEK1 nucleic acid molecule contains one or more mutations that confer resistance to a particular therapy, such as one or more RAF or MEK inhibitors. In a related embodiment, a mutant MEK1 nucleic acid molecule contains one or more mutations such that the mutant MEK1 nucleic acid molecule encodes a mutant MEK1 protein, wherein the mutant MEK1 protein contains one or more mutations that confer resistance to a particular therapy, such as one or more RAF or MEK inhibitors. Thus, in particular aspects of the invention, an alteration in a sequence results in a change that affects the properties of a protein encoded by the sequence such that at least some resistance to therapy, such as therapy with a RAF or MEK inhibitor, occurs as a result.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated nucleic acid segments and recombinant vectors incorporating DNA sequences that encode mutant MEK1 proteins or peptides that include within its amino acid sequence a contiguous amino acid sequence in accordance with, or essentially corresponding to mutant MEK1 proteins. In exemplary embodiments, the invention concerns isolated DNA segments and recombinant vectors incorporating DNA sequences that encode a MEK1 protein, polypeptide or peptide that includes within its amino acid sequence a contiguous amino acid sequence of a MEK1 protein comprising one or more mutations that confer resistance to one or more RAF or MEK inhibitors. In an exemplary embodiment, the mutations occurs at position 121, and preferably is a C121S substitution.

The nucleic acid segments used in the present invention, regardless of the length of the coding sequence itself, can be combined with other DNA or RNA sequences, such as promoters, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol.

It is contemplated that the nucleic acid constructs of the present invention encode a MEK1 protein or a mutant MEK1 protein. A "heterologous" sequence refers to a sequence that is foreign or exogenous to the remaining sequence. A heterologous gene refers to a gene that is not found in nature adjacent to the sequences with which it is now placed.

In a non-limiting example, one or more nucleic acid constructs can be prepared that include a contiguous stretch of nucleotides identical to or complementary to all or part of a MEK1 gene. A nucleic acid construct can comprise at least 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 20,000, 30,000, 50,000, 100,000, 250,000, about 500,000, 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, about 97001, about 1,001, about 1002, about 50,001, about 50,002, about 750,001, about 750,002, about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

Certain embodiments of the present invention concern various nucleic acids, including vectors, promoters, therapeutic nucleic acids, and other nucleic acid elements involved in transformation and expression in cells. In certain aspects, a nucleic acid comprises a wild-type or a mutant nucleic acid. In particular aspects, a nucleic acid encodes for or comprises a transcribed nucleic acid.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product. In addition to the MEK1 gene, other regulatory regions such as enhancers for MEK1 are contemplated as nucleic acids for use with compositions and methods of the claimed invention.

These definitions generally refer to a single-stranded molecule, but in specific embodiments will also encompass an additional strand that is partially, substantially or fully complementary to the single-stranded molecule. Thus, a nucleic acid can encompass a double-stranded molecule or a triple-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

A nucleic acid can be made by any technique known to one of ordinary skill in the art, for example, by chemical synthesis, or by enzymatic production or biological production. Non-limiting examples of a synthetic nucleic acid (e.g., a synthetic MEK1 primer that facilitates identification of a mutation conferring resistance to one or more RAF or MEK inhibitors), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotides can be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid includes one produced by enzymes in an amplification reactions such as PCR (see for example, U.S. Pat. Nos. 4,683,202 and 4,682,195, each incorporated herein by reference), or one produced by synthesis of oligonucleotides, as described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria.

A nucleic acid can be purified on polyacrylamide gels, cesium chloride centrifugation gradients, or by any other means known to one of ordinary skill in the art as part of assessment for a mutation that confers resistance to RAF and MEK inhibitors. In preferred aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, the bulk of cellular components or in vitro reaction components, including, for example, macromolecules such as lipids or proteins, small biological molecules, and the like.

V. Expression Vectors and Host Cells

The present invention encompasses expression vector compositions and the use of such vectors to encode for a MEK1 protein, e.g., a mutant MEK1 protein, as well as host cell compositions into which such expression vectors have been introduced. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques.

The term "expression vector" or "expression construct" refers to a vector containing a nucleic acid sequence coding for at least part of a gene product capable of being transcribed. In some cases, RNA molecules are then translated into a protein, protein, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors can contain nucleic acid sequences that serve other functions as well and are described infra.

1. Promoters and Enhancers

A "promoter" is a control sequence that is a region of a nucleic acid sequence at which initiation and rate of transcription are controlled. It can contain genetic elements at which regulatory proteins and molecules can bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter can be one naturally associated with a gene or sequence, as can be obtained by isolating the 5' non-coding sequences located upstream of the coding segment and/or exon. Such a promoter can be referred to as "endogenous." Similarly, an enhancer can be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers can include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression. The promoters employed can be constitutive, tissue-specific, inducible, and/or useful under the appropriate conditions to direct high level expression of the introduced DNA segment. The promoter can be heterologous or exogenous, for example, a non-MEK1 promoter with respect to MEK1 encoding sequence. In some examples, a prokaryotic promoter is employed for use with in vitro transcription of a desired sequence. Prokaryotic promoters for use with many commercially available systems include T7, T3, and Sp6.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements. In certain embodiments of the invention, the use of internal ribosome entry sites (IRES) elements are used to create multigene, or polycistronic, messages.

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences can require donor and/or acceptor splicing sites to ensure proper processing of the transcript for protein expression (see, for example, Chandler et al., 1997, herein incorporated by reference).

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

6. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence can be employed. Preferred embodiments include the SV40 polyadenylation signal and/or the bovine growth hormone polyadenylation signal, convenient and/or known to function well in various target cells. Polyadenylation can increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, the cells containing a nucleic acid construct of the present invention can be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) can be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Host Cells

As used herein, the terms "cell," "cell line," and "cell culture" may be used interchangeably. A cell comprising a MEK1 polynucleotide, either mutated or wild-type, can be employed in the invention. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. A "recombinant host cell" refers to a host cell that carries a recombinant nucleic acid, i.e. a nucleic acid that has been manipulated in vitro or that is a replicated copy of a nucleic acid that has been so manipulated.

A host cell can be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE™. Competent Cells and Solopack™ Gold Cells (Strategene®, La Jolla). Alternatively, bacterial cells such as *E. coli* LE392 could be used as host cells for phage viruses.

A preferred eukaryotic host cell of the invention is the melanoma cell line A375, wherein the cell has been transformed with an expression vector encoding a MEK1 protein, e.g., a mutant MEK1 protein of the invention.

10. Expression Systems

Numerous expression systems exist that comprise at least a part or all of the compositions discussed above. Prokaryote- and/or eukaryote-based systems can be employed for use with the present invention to produce MEK1 nucleic acid sequences, or their cognate proteins, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac™ 2.0 from Invitrogen™ and BacPack™ Baculovirus Expression System from Clontech™.

Other examples of expression systems include Stratagene's Complete Control Inducible Mammalian Expression System, which involves a synthetic ecdysone-inducible receptor, or its pET Expression System, an *E. coli* expression system. Another example of an inducible expression system is available from Invitrogen, which carries the T-Rex™ (tetracycline-regulated expression) System, an inducible mammalian expression system that uses the full-length CMV promoter. The Tet-On™ and Tet-Off™ systems from Clontech™ can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

Invitrogen also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate protein, protein, or peptide.

VI. Isolated Protein Molecules

Another aspect of the invention pertains to isolated and/or purified MEK1 proteins, and biologically active portions thereof. In particular aspects of the invention, the MEK1 proteins described herein comprise a mutation at amino acid position 121 conferring resistance to one or more RAF and/or MEK inhibitors. A "mutant MEK1 protein", as referenced herein, includes a MEK1 protein containing a mutation at amino acid position 121 that confers resistance to one or more known RAF and/or MEK inhibitors. Preferably, the isolated mutant MEK1 protein comprises a C121S mutation. In a preferred embodiment, the isolated mutant MEK1 protein comprises the amino acid sequence set forth in SEQ ID NO: 4.

An "isolated" or "purified" protein or biologically active portion thereof is substantially free of cellular material when produced by recombinant DNA techniques, or chemical precursors or other chemicals when chemically synthesized. The language "substantially free of cellular material" includes preparations of MEK1 proteins in which the protein is separated from cellular components of the cells in which it is naturally or recombinantly produced. In one embodiment, the language "substantially free of cellular material" includes preparations of MEK1 protein having less than about 30% (by dry weight) of non-MEK1 protein (also referred to herein as a "contaminating protein"), more preferably less than about 20% of non-MEK1 protein, still more preferably less than about 10% of non-MEK1 protein, and most preferably less than about 5% of non-MEK1 protein. When the MEK1 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of MEK1 protein in which the protein is separated from chemical precursors or other chemicals which are involved in the synthesis of the protein. In one embodiment, the language "substantially free of chemical precursors or other chemicals" includes preparations of MEK1 protein having less than about 30% (by dry weight) of chemical precursors or non-MEK1 chemicals, more preferably less than about 20% chemical precursors or non-MEK1 chemicals, still more preferably less than about 10% chemical precursors or non-MEK1 chemicals, and most preferably less than about 5% chemical precursors or non-MEK1 chemicals.

Biologically active portions of a MEK1 protein include peptides comprising amino acid sequences derived from the amino acid sequence of a MEK1 protein, e.g., the amino acid sequence shown in SEQ ID NOs:2 and 4, which include fewer amino acids than a full length MEK1 protein, and exhibit at least one activity of a MEK1 protein. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a MEK1 protein. Moreover, other biologically active portions, in which other regions of the protein are deleted, can be prepared by recombinant techniques and evaluated for one or more of the activities described herein. Preferably, the biologically active portions of a MEK1 protein include one or more selected domains/motifs or portions thereof having biological activity. In preferred embodiments, biologically active portions of a MEK1 protein comprise a mutation at amino acid position 121 with respect to a wild-type MEK1 sequence, wherein said mutation, when present in a full-length mutant MEK1 protein, confer resistance of the mutant MEK1 protein to known RAF and MEK inhibitors. In an exemplary embodiment, the mutation occurs at amino acid 121, preferably a C121S mutation.

MEK1 proteins are preferably produced by recombinant DNA techniques. For example, a nucleic acid molecule encoding the protein is cloned into an expression vector (as described above), the expression vector is introduced into a host cell (as described above) and the MEK1 protein is expressed in the host cell. The MEK1 protein can then be isolated from the cells by an appropriate purification scheme using standard protein purification techniques. Alternative to recombinant expression, a MEK1 protein, protein, or peptide can be synthesized chemically using standard peptide synthesis techniques. Moreover, a native MEK1 protein and/or a mutant MEK1 protein can be isolated from cells (e.g., cancer cells), for example using an anti-MEK1 antibody, which can be produced by standard techniques utilizing a MEK1 protein or fragment thereof of this invention.

The invention also provides MEK1 chimeric or fusion proteins. As used herein, a MEK1 "chimeric protein" or "fusion protein" comprises a MEK1 protein operatively linked to a non-MEK1 protein. A "MEK1 protein" refers to a protein having an amino acid sequence corresponding to a MEK1 protein, whereas a "non-MEK1 protein" refers to a protein having an amino acid sequence corresponding to a protein which is not substantially homologous to the MEK1 protein, e.g., a protein which is substantially different from the MEK1 protein, which does not display a MEK1 activity and which is derived from the same or a different organism. Within the fusion protein, the term "operatively linked" is intended to indicate that the MEK1 protein and the non-MEK1 protein are fused in-frame to each other. The non-MEK1 protein can be fused to the N-terminus or C-terminus of the MEK1 protein. For example, in one embodiment the fusion protein is a GST-MEK1 fusion protein in which the MEK1 sequences are fused to the C-terminus of the GST sequences. Such fusion proteins can facilitate the purification of recombinant MEK1 proteins. In another embodiment, the fusion protein is a MEK1 protein containing a heterologous signal sequence at its N-terminus. In certain host cells (e.g., mammalian host cells), expression and/or secretion of a MEK1 protein can be increased through use of a heterologous signal sequence.

Preferably, a MEK1 chimeric or fusion protein of the invention is produced by standard recombinant DNA techniques. For example, DNA fragments coding for the different protein sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST protein). A MEK1-encoding nucleic acid can be cloned into such an expression vector such that the fusion moiety is linked in-frame to the MEK1 protein.

In a preferred embodiment, the isolated MEK1 proteins of the invention contain one or more mutations (e.g., substitutions or deletions) with respect to a wild-type MEK1 protein sequence. In one embodiment, the mutant MEK1 proteins contain one or more mutations with respect to a human wild-type MEK1 protein sequence (SEQ ID NO:2). In a particularly preferred embodiment, the one or more mutations confer resistance to one or more RAF and/or MEK inhibitors. In an exemplary embodiment, the RAF inhibitor is PLX4032 and/or PLX4720 and the MEK inhibitor is AZD6244. A mutant MEK1 protein of the invention exhibits a biological activity characteristic of a wild-type MEK1 protein. Such a biological activity can include, for example, phosphorylation of ERK1/2. Exemplary mutant MEK1 proteins of the invention include MEK1 proteins comprising a mutation at amino acid position 121, preferably a C121s mutation.

Mutant MEK1 proteins can be generated by mutagenesis of a wild-type MEK1 protein, or of the nucleic acid molecule encoding a wild-type MEK1 protein. Mutant MEK1 proteins can also be identified by screening combinatorial libraries of MEK1 mutants for a mutant MEK1 protein having a desired activity, e.g., resistance to one or more RAF and/or MEK inhibitors. Several techniques are known in the art for screening gene products of combinatorial libraries made by point mutations or truncation, and for screening cDNA libraries for gene products having a selected property. Such techniques are adaptable for rapid screening of the gene libraries generated by combinatorial mutagenesis. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

VIII. Detection of Mutations

In another aspect, the invention pertains to methods of detecting the presence of a mutant MEK1 protein in a sample (e.g., a biological sample from a cancer patient). A variety of screening methods can be used to detect the presence of a mutant MEK1 protein of the invention in a sample, e.g., a nucleic acid and/or a protein sample. In specific embodiments, the sample contains a cell or cell extract. In exemplary embodiments, the sample is obtained from a subject, e.g., a subject having cancer.

Methods for detecting the presence of resistance mutations in genomic DNA, cDNA, and RNA (i.e., mRNA) containing a sequence encoding a MEK1 protein, or biologically active portion thereof, can be used within the scope of the present invention. Likewise, methods for detecting the presence of resistance mutations in MEK1 proteins, or biologically active portions thereof, can be used within the scope of the present invention. In particular embodiments, methods including, but not limited to, the following can be used to detect the presence of a MEK1 protein, or a nucleic acid molecule encoding a MEK1 protein, having a mutation at amino acid position 121 as compared to the wild-type MEK1 (SEQ ID NO: 2).

Point mutations can be detected using any suitable method known in the art, including, for example, denaturing gradient gel electrophoresis ("DGGE"), restriction fragment length polymorphism analysis ("RFLP"), chemical or enzymatic cleavage methods, direct sequencing of target regions amplified by PCR (see above), single-strand conformation polymorphism analysis ("SSCP"), polymerase chain reaction, sequencing, hybridization, or "hybrid capture" followed by pyrosequencing or single-molecule sequencing. One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations. U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. For example, Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that can be used in the practice of the present invention are disclosed in U.S. Pat. Nos. 5,849,483, 5,851,770, 5,866,337, 5,925,525 and 5,928,870, each of which is incorporated herein by reference in its entirety.

Screening methods can be performed to screen an individual for the occurrence of the mutations identified above. For example, in one embodiment, a sample (such as blood or other bodily fluid or cell or tissue sample) is taken from a patient for analysis. In an exemplary embodiment, the patient is a cancer patient. Methods suitable for processing such samples for detection of a mutation in a MEK1 nucleic acid or a MEK1 protein are known in the art, and the skilled artisan may adapt the processing of such samples in accordance with the chosen method of detection. For example, when detecting the presence of mutations in a nucleic acid encoding a MEK1 protein, biological samples (e.g., cell samples or tissue samples) may be processed such that the nucleic acid material in the sample is accessible to reagents used to detect mutations (e.g., nucleic acid probes, primers, etc.). Accordingly, in certain embodiments, the nucleic acid material in a biological sample is extracted from cells within the sample. "Extraction" of nucleic acid material as used herein refers to the process of making the nucleic acid material in a biological sample accessible to contact by reagents used for detection. For example, in a cell sample, the nucleic acid material (e.g., mRNA encoding a MEK1 protein, DNA encoding a MEK1 protein, etc.) is located inside the cell membrane, making it inaccessible by detection reagents added to the sample. Accordingly, extraction of the nucleic acid material by disrupting the integrity of the cell membrane is commonly employed. Exemplary means of extracting nucleic acid material from a cell are known in the art and include, but are not limited to, mechanical disruption (e.g., sonication, French press, vortexing, Dounce homogenization, etc.), and/or detergent-mediated disruption (e.g., disruption in lysis buffer containing detergents such as Triton-X-100, CHAPS, SDS, etc.). Depending on the method of detection, the nucleic acid material may or may not be isolated from other components of the sample during or following extraction. For example, for detection methods employing PCR amplification of a nucleic acid molecule encoding a MEK1 protein, nucleic acid material that has been extracted from cells may be used without further isolation (e.g., as a component of a crude lysate). In one embodiment, a biological sample may be isolated on filter paper that is then processed using standard extraction techniques prior to PCR amplification of a nucleic acid molecule encoding a MEK1 protein. Such filter paper can contain chemical reagents that lyse cells, and can additionally contain reagents that stabilize and protect nucleic acid material (e.g., Whatman FTA™, GE Healthcare). PCR amplification of a MEK1 nucleic acid molecule may be performed from samples stored on filter paper without isolation from other cellular components. In other embodiments, nucleic acid material may be isolated from other non-nucleic acid components in the sample using techniques known in the art. As described therein, modifications to the methods of extraction and/or isolation may be used depending on the type of nucleic acid material to be assayed (e.g. DNA or RNA). Methods of detecting mutations in a MEK1 protein also may employ extraction and/or isolation of proteins from a biological sample. Techniques suitable for extracting and/or isolating proteins from a biological sample are well known in the art.

The presence or absence of one or more mutations described herein determines the ability of the screened individuals to resist therapy with a RAF inhibitor and/or a first-generation MEK1 inhibitor. According to methods provided by the invention, these results will be used to adjust and/or alter the dose of the RAF inhibitor and/or the first-generation MEK1 inhibitor, or to select a course of treatment using a second-generation MEK1 inhibitor. Effective treatment of a subject having cancer can comprise the eradication of a cancer cell, the cessation or reduction of cancer (such as solid tumor) growth rate, or the amelioration of at least one cancer symptom.

The resistance mutations in MEK1 proteins, or in nucleic acid molecules encoding MEK1 proteins, can be detected using any suitable methods known in the art, or modifications thereof, including the methods described below. Such methods include the use of allele-specific polymerase chain reaction, direct or indirect sequencing of the site, the use of restriction enzymes where the respective alleles of the site create or destroy a restriction site, the use of allele-specific hybridization probes, the use of antibodies that are specific for mutant MEK1 proteins, or any other biochemical interpretation.

1. DNA Sequencing

The most commonly used method of characterizing a mutation is direct DNA sequencing of the genetic locus that flanks and includes the polymorphism. Such analysis can be accomplished using either the "dideoxy-mediated chain termination method," also known as the "Sanger Method" (Sanger, F., et al., 1975) or the "chemical degradation method," also known as the "Maxam-Gilbert method" (Maxam, A. M., et al., 1977). Sequencing in combination with genomic sequence-specific amplification technologies, such as the polymerase chain reaction, can be utilized to facilitate the recovery of the desired genes (Mullis, K. et al., 1986; European Patent Appln. 50,424; European Patent Appln. 84,796, European Patent Application 258,017, European Patent Appln. 237,362; European Patent Appln. 201, 184; U.S. Pat. Nos. 4,683,202; 4,582,788; and 4,683,194), all of which are incorporated herein by reference. Sequencing of pooled samples can also be accomplished using Solexa/Illumina sequencing (Illumina,® San Diego, Calif.), pyrosequencing, or other single-molecule sequencing approaches. In one embodiment, mutations in the MEK1 gene can be detected by cloning and sequencing a MEK1 allele present in a sample obtained from the subject. If desired, MEK1 mRNA can be sequenced directly, or the polymerase chain reaction technique ("PCR") can be used to amplify MEK1 DNA or mRNA to produce encoding DNA ("cDNA"), and the resultant cDNA can be sequenced. PCR can also be used to selectively amplify a region of the MEK1 allele.

2. Exonuclease Resistance

Other methods that can be employed to determine the identity of a nucleotide present at a mutated site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known, one can determine the specific nucleotide present in the polymorphic site of the DNA.

3. Microsequencing Methods

Several other primer-guided nucleotide incorporation procedures have been described (Komher, J. S. et al., 1989; Sokolov, B. P., 1990; Syvanen 1990; Kuppuswamy et al., 1991; Prezant et al., 1992; Ugozzoll, L. et al., 1992; Nyren et al., 1993). These methods rely on the incorporation of labeled deoxynucleotides to discriminate between bases at a mutated site. As the signal is proportional to the number of deoxynucleotides incorporated, mutations that occur in runs of the same nucleotide result in a signal that is proportional to the length of the run (Syvanen et al., 1993).

4. Extension in Solution

French Patent 2,650,840 and PCT Application No. WO91/02087 discuss a solution-based method for determining the identity of the nucleotide of a mutated site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

5. Genetic Bit™ Analysis or Solid-Phase Extension

PCT Appln. No. 92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here, the primer or the target molecule is immobilized to a solid phase.

6. Oligonucleotide Ligation Assay (OLA)

Oligonucleotide Ligation Assay is a solid phase method that uses different methodology than that described above (Landegren et al., 1988). Two oligonucleotides capable of hybridizing to abutting sequences of a single strand of a target DNA are utilized. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide using avidin. Other nucleic acid detection assays, based on this method, combined with PCR are also described (Nickerson et al., 1990). Here, PCR is used to achieve the exponential amplification of target DNA, which is then detected using the OLA.

7. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone, and unlike the polymerase-based assays, this method enhances the specificity of the polymerase step by combining it with a second hybridization and a ligation step for a signal to be attached to the solid phase.

8. Methods of Nucleic Acid Transfer

For some methods of the present invention, methods of nucleic acid transfer can be employed. Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945, 100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat.

Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); or by desiccation/inhibition-mediated DNA uptake (Potrykus et al., 1985). Through the application of techniques such as these, organelle(s), cell(s), tissue(s) or organism(s) can be stably or transiently transformed.

9. Allele-Specific Antibodies

MEK1 proteins having a resistance mutation described herein can be detected using antibodies that specifically recognize the mutant MEK1 protein, but do not recognize wild-type MEK1 protein. Antibodies can be raised against one or more allelic forms of the MEK1 protein having one or more resistance mutations. Techniques for using a specific protein or an oligopeptide as an antigen to elicit antibodies that specifically recognize epitopes on the peptide or protein are well known. In one embodiment, the DNA sequence of the desired allelic form of the target gene can be cloned by insertion into an appropriate expression vector and translated into protein in a prokaryotic or eukaryotic host cell. The protein can be recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. A third embodiment is to use the DNA sequence of the alternative alleles as a basis for the generation of synthetic peptides representing the amino acid sequence of the alleles for use as antigen to elicit the production of specific antibodies.

Antibodies can be generated either by standard monoclonal antibody techniques or generated through recombinant based expression systems. The term "antibodies" is meant to include intact antibody molecules as well as antibody fragments or derivatives, such as Fab and F(ab')2, which are capable of specifically binding to antigen. The antibodies so produced will preferentially bind only the mutant protein produced in the allelic form which was used as an antigen to create the antibody. Methods of generating allele-specific antibodies are also described in U.S. Pat. No. 6,200,754 and U.S. Pat. No. 6,054,273, the entire contents of which are incorporated herein by reference.

Such antibodies specific for mutant MEK1 proteins can be used to detect the presence of a MEK1 protein having one or more resistance mutations in a sample, e.g., an assay sample, a cell sample, a cell extract, a biological sample, or a patient sample, using techniques known in the art. These techniques include, for example, Western blot, immunohistochemistry, indirect immunofluorescence, and antibody microarray. Antibodies which specifically recognize mutant MEK1 proteins can also be second-generation MEK1 inhibitors. The ability of an antibody which specifically recognizes a mutant MEK1 protein to inhibit the biological activity of the mutant MEK1 protein can be determined using the methods described herein for identifying second-generation MEK1 inhibitors.

IX. Diagnostic and Screening Applications

The foregoing techniques can be used to determine the presence or absence of a previously identified resistance mutation in a MEK1 nucleic acid or protein molecule in a sample obtained from a patient. Identification of a mutant MEK1 nucleic acid or protein molecule in a patient sample can be useful for characterizing a disease or condition in the patient. For example, in a patient having a disease associated with aberrant expression or activation of MEK1 (e.g., a cancer), identification of a mutant MEK1 nucleic acid or protein molecule in sample (e.g., a cancer-cell containing sample) obtained from the patient indicates that the patient is at a relatively high risk of relapse or lack of response to treatment with a RAF or MEK inhibitor. In one embodiment, identification of a MEK1 nucleic acid or protein molecule containing one or more mutations described herein in a cancer-cell containing sample obtained from a patient indicates that the patient is at a relatively high risk of relapse or lack of response to treatment with a RAF inhibitor, such as PLX4032 or PLX4720, or with a first generation MEK inhibitor, e.g., CI-1040, AZD6244, PD318088, PD98059, PD334581, RDEA119, Compound A, or Compound B.

A patient who has a MEK1 resistance mutation described herein has a higher risk of relapse from treatment with a RAF inhibitor or a first-generation MEK inhibitor than a patient in whom a MEK1 resistance mutation cannot be detected. Accordingly, as used herein, the term "relatively high risk of relapse" is in relation to a patient in whom a mutant MEK1 nucleic acid or protein molecule cannot be detected. That is, a patient who has a "relatively high risk of relapse" is a patient who has a greater risk of relapse as compared to a patient in whom a mutant MEK1 nucleic acid or protein molecule cannot be detected.

In certain embodiments, identification of a MEK1 protein, or a nucleic acid encoding a MEK1 protein, having a mutation at amino acid position 121 of wild-type MEK1 shown in SEQ ID NO: 2, indicates that the patient is at relatively high risk of relapse or lack of response to treatment with a RAF inhibitor and/or a first-generation MEK inhibitor.

Determining the presence or absence of a mutant MEK1 nucleic acid or protein molecule in a patient sample also allows for the selection of an optimized treatment regimen for the patient, or stratification of the patient to a certain treatment group. In one embodiment, a treatment regimen comprising treatment with a RAF inhibitor and/or a first-generation MEK inhibitor is selected for a patient wherein a cancer cell-containing sample from the patient does not contain a mutant MEK1 nucleic acid or protein molecule. Such a patient can be stratified to a treatment regimen comprising a RAF inhibitor and/or a first-generation MEK inhibitor. The RAF and/or MEK inhibitor can be given to such a patient at a standard dosage, at standard dosing intervals.

In another embodiment, a treatment regimen comprising a combination therapy with a MEK inhibitor and a RAF inhibitor is selected for a patient wherein a cancer cell-containing sample from the patient does not contain a mutant MEK1 nucleic acid or protein molecule. Such a patient can be stratified to a treatment regimen comprising a first generation MEK inhibitor or a second generation MEK inhibitor, in combination with a RAF inhibitor. A treatment regimen comprising a combination therapy with a RAF inhibitor and a MEK inhibitor that targets the C121S MEK1 mutation advantageously suppresses the emergence of MEK resistant alleles in a patient whose cancer does not contain a mutant MEK1 molecule.

In another embodiment, a treatment regimen comprising treatment without a MEK inhibitor is selected for a patient wherein a cancer cell-containing sample from the patient contains a mutant MEK1 nucleic acid or protein molecule, e.g., a MEK1 nucleic acid or protein molecule containing one or more of the mutations described herein. Such a patient can be stratified to a treatment regimen that does not comprise a MEK inhibitor.

In an alternative embodiment, identification of a mutant MEK1 nucleic acid or protein molecule, wherein the mutant MEK1 comprises a C121S mutation, in a cancer-cell containing sample obtained from a patient indicates that the patient is likely to respond to treatment with a second-generation MEK inhibitor that targets a MEK1 mutant comprising a C121S mutation. Accordingly, in one embodiment, a treatment regimen comprising treatment with a second-generation MEK inhibitor that targets a C121S mutant MEK1 protein is selected for a patient wherein a cancer cell-containing sample from the patient contains a mutant MEK1 nucleic acid or protein molecule comprising the C121S mutation. Such a patient can be stratified to a treatment regimen comprising such a second-generation MEK inhibitor.

The practice of the present invention will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

X. Methods of Treatment

In various embodiments, the invention provides methods of treating a subject having a cancer. Said methods generally comprise administration of a MEK1 inhibitor, e.g., a second-generation MEK1 inhibitor, as described herein, that targets a mutant MEK1 having a substitution at amino acid position 121 as compared to the wild-type MEK1 of SEQ ID NO: 2 (.e.g., a C121S mutation). In an exemplary embodiment, the subject has a cancer containing a mutant MEK1 protein having a resistance mutation as described herein. In related embodiments, the subject has a cancer containing a nucleic acid molecule encoding a MEK1 protein having a resistance mutation as described herein. The term "treated," "treating" or "treatment" includes the diminishment or alleviation of at least one symptom associated with the condition being treated. For example, treatment can be diminishment of one or several symptoms of a disorder or complete eradication of a disorder, such as cancer.

In an exemplary embodiment, the cancer is a melanoma, such as a metastatic melanoma. In other exemplary embodiments, the cancer is selected from the group consisting of leukemias, lymphomas, myelomas, carcinomas, metastatic carcinomas, sarcomas, adenomas, nervous system cancers and geritourinary cancers. However, because mutations in MEK1 broadly enhance resistance in a number of types of cancer, the methods and second-generation MEK1 inhibitors described herein are useful in treating a broad spectrum of tumors, including all solid tumors and hematological malignancies. Examples of such tumors include but are not limited to leukemias, lymphomas, myelomas, carcinomas, metastatic carcinomas, sarcomas, adenomas, nervous system cancers and geritourinary cancers. In exemplary embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

In some embodiments, pharmaceutical compositions of the compounds (or combinations) of the invention can be in unitary dosage form suitable for administration orally, rectally or by parenteral injection. For example, in preparing compositions in oral dosage form, any of the usual pharmaceutical media may be employed, such as, for example, water, glycols, oils, alcohols and the like, as in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are employed. For parenteral compositions, carriers usually comprise sterile water, at least in large part, though other ingredients, for example, to aid solubility, may be included. Injectable solutions, for example, are prepared using a carrier which comprises saline solution, glucose solution or a mixture of saline and glucose solution. Injectable suspensions may also be prepared in which case appropriate liquid carriers, suspending agents and the like may be employed. In case of compositions suitable for percutaneous administration, carrier optionally comprises a penetration enhancing agent and/or a suitable wetting agent, which may be combined with suitable additives of any nature in minor proportions, which additives do not cause a significant deleterious effect to the skin. Additives may facilitate the administration to the skin and/or may be helpful for preparing desired compositions. These compositions may be administered in various ways, e.g., as a transdermal patch, as a spot-on, as an ointment.

It is especially advantageous to formulate the pharmaceutical compositions described herein in dosage unit form for ease of administration and uniformity of dosage. Dosage unit form, as used herein, refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof In general it is contemplated that a therapeutically effective amount of a first or a second compound would be from about 0.0001 mg/kg to 0.001 mg/kg; 0.001 mg/kg to about 10 mg/kg body weight or from about 0.02 mg/kg to about 5 mg/kg body weight. In some embodiments, a therapeutically effective amount of a first or a second compound is from about 0.007 mg to about 0.07 mg, about 0.07 mg to about 700 mg, or from about 1.4 mg to about 350 mg. A method of prophylactic or curative treatment may also include administering the composition in a regimen of between one to five intakes per day.

In some embodiments, a therapeutically effective amount of a first compound or a second compound includes, but is not limited to, the amount less than about 0.01 mg/dose, or less than about 0.5 mg/dose, or less than about 1 mg/dose, or less than about 2 mg/dose, or less than about 5 mg/dose, or less than about 10 mg/dose, or less than about 20 mg/dose, or less than about 25 mg/dose, or less than about 50 mg/dose, or less than about 100 mg/dose. The number of times a day a first or a second compound is administrated to a subject can be determined based on various criteria commonly used in the art and/or those described herein.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the composition that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a composition of the present invention with the carrier and, optionally, one or more accessory ingredients. In general, the formulations are prepared by uniformly and intimately bringing into association a composition of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a composition of the present invention as an active ingredient. A composition of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compositions of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compositions, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compositions of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active composition.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a composition of this invention include powders, sprays, ointments, pastes, creams, lotions, gels, solutions, patches and inhalants. The active composition may be mixed under sterile conditions with a pharmaceutically acceptable carrier, and with any preservatives, buffers, or propellants that may be required.

The ointments, pastes, creams and gels may contain, in addition to an active composition of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a composition of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a composition of the present invention to the body. Such dosage forms can be made by dissolving or dispersing the composition in the proper medium. Absorption enhancers can also be used to increase the flux of the composition across the skin. The rate of such flux can be controlled by either providing a rate controlling membrane or dispersing the active composition in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compositions of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compositions in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount can be, for example, an amount that inhibits growth of tumor cells in the subject.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

XI. Methods of Treatment Using a Combination Therapy

The present invention further describes methods of suppressing the emergence of MEK1 resistance mutations in a subject having cancer. Such methods involve the combined administration of a RAF inhibitor and a second generation MEK1 inhibitor that targets a mutant MEK1 protein having a substitution at amino acid position 121 as compared to wild-type MEK1 of SEQ ID NO: 1. Preferably, the second generation MEK1 inhibitor targets a mutant MEK1 protein having a C121S substitution. Accordingly, the present invention provides a combination therapy for treating or preventing the symptoms of a cancer, comprising administration of a RAF inhibitor and a MEK1 inhibitor that targets a mutant MEK1 protein having a substitution at amino acid position 121 as compared to wild-type MEK1 of SEQ ID NO: 1 (preferably a C121S mutation). The term "combination therapy", as used herein, refers to the administration of two or more therapeutic substances, e.g., a MEK1 inhibitor or a RAF inhibitor. The MEK1 inhibitor may be administered concomitant with, prior to, or following the administration of a RAF inhibitor. As set forth herein, a combination therapy involving a second generation MEK1 inhibitor and a RAF inhibitor suppresses the emergence of MEK resistance mutations to a greater extent than administration of either a MEK1 inhibitor or a RAF inhibitor alone. Standard dosages of the second generation MEK1 inhibitor and RAF inhibitors are also suitable for the combination therapies described herein. Exemplary cancers that can be treated with a combination therapy include those described herein, for example, melanoma, leukemias, lymphomas, myelomas, carcinomas, metastatic carcinomas, sarcomas, adenomas, nervous system cancers and geritourinary cancers, e.g., melanoma, myelodysplastic syndrome, leukemia, pancreatic cancer, ovarian cancer, peritoneal cancer, non small cell lung cancer, and breast cancer.

Second generation MEK1 inhibitors that target a mutant MEK1 protein having a substitution at amino acid position 121 as compared to wild-type MEK1 of SEQ ID NO: 1 (preferably a C121S mutation) can be identified as described herein. Exemplary RAF inhibitors useful for combination therapy include pan-RAF inhibitors, inhibitors of B-RAF, inhibitors of A-RAF, and inhibitors of RAF-1. In exemplary embodiments RAF inhibitors useful for combination therapy include PLX4720, PLX4032, BAY 43-9006 (Sorafenib), ZM 336372, RAF 265, AAL-881, LBT-613, and CJS352. Exemplary RAF inhibitors further include the compounds set forth in PCT Publication No. WO/2008/028141, the entire contents of which are incorporated herein by reference. Exemplary RAF inhibitors additionally include the quinazolinone derivatives described in PCT Publication No.

WO/2006/024836, and the pyridinylquinazolinamine derivatives described in PCT Publication No. WO/2008/020203, the entire contents of which are incorporated herein by reference.

Accordingly, the invention provides methods of treating cancer in a subject, comprising administering a combination therapy comprising a second generation MEK1 inhibitor and a RAF inhibitor, as described herein. In some embodiments, the method further comprises screening a subject to detect the presence or absence of one or more mutations in MEK1. In a preferred embodiment, a combination therapy comprising a second generation MEK inhibitor and a RAF inhibitor is selected for a subject in whom one or more mutations in MEK1 are not detected. In such a subject, the combination therapy advantageously suppresses the emergence of MEK1 resistance mutations. The invention further provides methods of suppressing the emergence of MEK1 resistance mutations in a subject having cancer, comprising administering to the subject a combination therapy comprising a second generation MEK1 inhibitor and a RAF inhibitor, as described herein. Accordingly, a combination therapy comprising a second generation MEK1 inhibitor and a RAF inhibitor may be administered to a subject in whom one or more MEK1 resistance mutations are detected. Such a combination therapy suppresses the growth of cells containing MEK1 resistance mutations. In some embodiments, the method further comprises screening a subject to detect the presence or absence of one or more mutations in MEK1. In these embodiments, a combination therapy comprising a second generation MEK1 inhibitor and a RAF inhibitor can be given, for example, to a subject in whom a MEK1 resistance mutation was not detected, or, for example, to a subject in whom a MEK1 resistance mutation was detected.

In another embodiment of the invention, a pharmaceutical composition can comprise (a) a second generation MEK1 inhibitor that targets a mutant MEK1 protein having a substitution at amino acid position 121 as compared to wild-type MEK1 of SEQ ID NO: 1 (preferably a C121S mutation) and also (b) a RAF inhibitor. In some embodiments, the RAF inhibitor can be a pan-RAF inhibitor, an inhibitor of B-RAF, an inhibitor of A-RAF, and an inhibitor of RAF-1. In preferred embodiments, the RAF inhibitor can be PLX4720, PLX4032, BAY 43-9006 (Sorafenib), ZM 336372, RAF 265, AAL-881, LBT-613, and CJS352. In a particular embodiment, the RAF inhibitor is (a) PLX4720 or PLX4032.

Another embodiment of the invention is directed to methods of administering the pharmaceutical compositions described herein. Hence, the present invention is directed to a method of treating a subject for cancer comprising administering to the subject a second generation MEK1 inhibitor that targets a mutant MEK1 protein having a substitution at amino acid position 121 as compared to wild-type MEK1 of SEQ ID NO: 1 (preferably a C121S mutation); and administering to the subject a pharmaceutical composition comprising a RAF inhibitor. The second generation MEK1 inhibitor and the RAF inhibitor can be administered to the subject sequentially or simultaneously. A sequential administration includes (a) first administering the second generation MEK1 inhibitor followed by (b) administering the RAF inhibitor. An alternative sequential administration includes (a) first administering the RAF inhibitor followed by (b) administering the second generation MEK1 inhibitor. A simultaneous administration includes administering the second generation MEK1 inhibitor and the RAF inhibitor at the same time; or at substantially the same time.

When administration involves the separate administration (e.g., sequential administration) of the first compound (e.g., a second generation MEK1 inhibitor) and a second compound (e.g., a RAF inhibitor), as described herein, the compounds are administered sufficiently close in time to have the desired therapeutic effect. For example, the period of time between each administration, which can result in the desired therapeutic effect, can range from minutes to hours and can be determined based on the properties of each compound such as potency, solubility, bioavailability, plasma half-life and kinetic profile. For example, the compounds can be administered in any order within about 24 hours of each other or within any time less than 24 hours of each other.

When the second generation MEK1 inhibitor and the RAF inhibitor are administered sequentially, they are separately formulated and can be provided in any order. When the second generation MEK1 inhibitor and the RAF inhibitor are administered simultaneously, however, they may be either separately formulated or combined in the same formulation. When combined in the same formulation, the second generation MEK1 inhibitor and the RAF inhibitor can be formulated so as to be released into the subject at the same time or at different times. The release profile of a formulation comprising both the second generation MEK1 inhibitor and the RAF inhibitor includes the following:
  A) release and bioavailability of the second generation MEK1 inhibitor followed by release and bioavailability of the RAF inhibitor;
  B) release and bioavailability of the RAF inhibitor followed by release and bioavailability of the second generation MEK1 inhibitor;
  C) release and bioavailability of the second generation MEK1 inhibitor at the same time (or substantially at the same time as) release and bioavailability of the RAF inhibitor.

In another embodiment, provided herein is a method of treating cancer in a subject in need thereof comprising administering to the subject a composition comprising a second generation MEK1 inhibitor and a RAF inhibitor. In still another embodiment, provided herein is a method of treating cancer in a subject in need thereof comprising administering to the subject a composition comprising a second generation MEK1 inhibitor and a RAF inhibitor, wherein the cancer is selected from the group consisting of melanoma, leukemias, lymphomas, myelomas, carcinomas, metastatic carcinomas, sarcomas, adenomas, nervous system cancers and geritourinary cancers, e.g., melanoma, myelodysplastic syndrome, leukemia, pancreatic cancer, ovarian cancer, peritoneal cancer, non small cell lung cancer, and breast cancer.

A combination of compounds described herein (e.g., a second generation MEK1 inhibitor and a RAF inhibitor) can either result in synergistic increase in anti-cancer activity, or such an increase can be additive. Compositions described herein typically include lower dosages of each compound in a composition, thereby avoiding adverse interactions between compounds and/or harmful side effects, such as ones which have been reported for similar compounds. Furthermore, normal amounts of each compound when given in combination could provide for greater efficacy in subjects who are either unresponsive or minimally responsive to each compound when used alone. For example, when given in combination, a second generation MEK1 inhibitor and a RAF inhibitor suppress the emergence of MEK1 resistance alleles to a greater extent than when either compound is used alone.

A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In certain embodiments, the invention provides a pharmaceutical composition of any of the compositions of the present invention. In a related embodiment, the invention provides a pharmaceutical composition of any of the compositions of the present invention and a pharmaceutically acceptable carrier or excipient of any of these compositions.

In one embodiment, the invention includes a packaged cancer treatment. The packaged treatment includes a composition of the invention packaged with instructions for using an effective amount of the composition of the invention for an intended use. In other embodiments, the present invention provides a use of any of the compositions of the invention for manufacture of a medicament to treat a cancer in a subject.

In another embodiment of the invention, the second generation MEK1 inhibitor and the RAF inhibitor can be administered sequentially (in any order) or simultaneously with other pharmaceutical agents typically administered to subjects being treated for cancer. Such other pharmaceutical agents include without limitation anti-emetics, agents that increase appetite, other cytotoxic or chemotherapeutic agents, and agents that relieve pain.

XII. Kits

Various kits may be assembled as part of the present invention. A kit can contain components to assay for mutations in MEK1 to evaluate a particular patient for the risk of developing resistance to therapy using one or more RAF inhibitors and/or MEK inhibitor, and thus allow a clinician to determine whether an alternative treatment for the patient is needed. Such kits can contain reagents that allow for mutations to be evaluated, such as primer sets to evaluate mutations correlated with relevant phenotypic manifestations concerning resistance to a RAF inhibitor and/or a MEK inhibitor. It is contemplated that primers (or pairs of primers) that are complementary to or identical to all or part of SEQ ID NO:1, encoding wild-type human MEK1, for example, can be part of a kit. In preferred embodiments, the primers can be used to specifically detect or amplify a nucleic acid molecule encoding a mutant MEK1 protein containing a mutation at amino acid position 121, such as a C121S mutation. In other embodiments, the kits contain instructions for using primers that are complementary or identical to all or part of SEQ ID NO:1 to amplify a nucleotide sequence encoding a MEK1 protein.

In other embodiments, the kits comprise compositions for detecting a mutation comprising a MEK1 protein, such as an antibody which specifically recognizes a mutant MEK1 protein containing a resistance mutation. Exemplary proteins include a mutant MEK1 protein containing a mutation at amino acid position 121, such as a C121S mutation.

All of the essential materials and reagents required for assaying for MEK1 mutations by a particular method discussed above can also be assembled together in a kit. When the components of the kit are provided in one or more liquid solutions, the liquid solution preferably is an aqueous solution, with a sterile aqueous solution being particularly preferred.

The invention further provides kits comprising compositions, (e.g., pharmaceutical compositions), comprising a second generation MEK1 inhibitor that targets a mutant MEK1 protein having a mutation at amino acid position 121 as compared to the wild-type MEK1 of SEQ ID NO: 2, such as the C121S mutation. Such kits can be used in the methods set forth herein, for example, for treating a cancer in a subject. Accordingly, the kits may further contain instructions that describe the use of the composition for the treatment of cancer.

The invention likewise provides kits comprising compositions suitable for use in a combination therapy involving a second generation MEK1 inhibitor that targets a mutant MEK1 protein having a mutation at amino acid position 121 as compared to the wild-type MEK1 of SEQ ID NO: 2, such as the C121S mutation, and a RAF inhibitor. Such kits may include, for example, a composition comprising a second generation MEK1 inhibitor and a composition comprising a RAF inhibitor. Such kits may alternatively include a composition comprising both a second generation MEK1 inhibitor and a RAF inhibitor. The kits may further contain instructions that describe the use of the composition for the treatment of cancer, and/or for suppressing the emergence of MEK1 resistance alleles in a subject having cancer. The instructions may describe the administration of a composition comprising a second generation MEK1 inhibitor simultaneously, prior to, or following administration of a RAF inhibitor.

The components of the kit can also be provided in dried or lyophilized forms. When reagents or components are provided as a dried form, reconstitution generally is by the addition of a suitable solvent. It is envisioned that the solvent also can be provided in another container means.

The kits of the present invention also will typically include a means for containing the vials in close confinement for commercial sale such as, e.g., injection or blow-molded plastic containers into which the desired vials are retained. Irrespective of the number or type of containers, the kits of the invention also can comprise, or be packaged with, an instrument for assisting with sample collection and evaluation. Such an instrument can be an inhalant, syringe, pipette, forceps, measured spoon, eye dropper or any such medically approved delivery vehicle, for example.

The kits of the invention can also include an instruction sheet outlining suggested alternative therapies when particular mutations are identified in a patient. For example, an instruction sheet included with the kits of the invention can recommend that a patient having a disorder, e.g., a cancer, in which a mutant MEK1 protein has been identified, discontinue treatment with a first-generation MEK1 inhibitor and/or a RAF inhibitor, be monitored for relapse during treatment with a first-generation MEK1 inhibitor and/or a RAF inhibitor, continue treatment with a first-generation MEK1 inhibitor and/or a RAF inhibitor at an elevated dosage, or initiate treatment with a second-generation MEK1 inhibitor, alone or in combination with a RAF inhibitor. An instruction sheet included with the kits of the invention can likewise recommend that a patient having a disorder in which a mutant MEK1 protein is not detectable continue treatment with a first-generation MEK1 inhibitor and/or a RAF inhibitor at a standard dosage. In exemplary embodiments, the first-generation MEK inhibitor is CI-1040, AZD6244, PD318088, PD98059, PD334581, RDEA119, Compound A, or Compound B.

This invention is further illustrated by the following examples, which should not be construed as limiting. The contents of all references, patents and published patent applications cited throughout this application are incorporated herein by reference.

EXAMPLES

Example 1: Identification of Activating MEK1 C121S Mutation

In this example, DNA samples from a patient with metastatic melanoma who developed resistance to the BRAF inhibitor PLX4032 were used to identify an activating MEK1 mutation that conferred resistance to both BRAF and MEK1 inhibitors. More specifically, massively parallel sequencing was used to conduct a comparative genomic analysis of 3 different DNA samples from the patient: (i) tumor that was sensitive to PLX4032, (ii) tumor that was resistant to PLX4032, and (iii) normal skin, to thereby allow for the identification of the activating MEK1 mutation.

The patient was a 38 year old man who was diagnosed with metastatic melanoma in February 2009. He initially presented with a mass in his right axilla, and a staging PET-CT demonstrated a large lesion in the right latissimus dorsi as well as multiple hypermetabolic foci in the lungs, liver, bones and several subcutaneous sites. Biopsy of the latissimus dorsi mass showed malignant melanoma. He was treated with several therapeutic regimens with minimal clinical response. By October 2009, the patient had developed numerous subcutaneous metastatic deposits. Genotyping of the BRAF oncogene at this time demonstrated a V600E mutation, and he enrolled in a clinical trial of the specific BRAF inhibitor PLX4032. The patient had a profound response to therapy, with a visible partial response within 2 weeks of starting PLX4032 and near complete regression of all visible tumor nodules by January 2010, after 15 weeks of therapy.

In late February 2010, after 4 months of therapy with PLX4032, the patient rapidly developed new subcutaneous nodules all over his body and PLX4032 was stopped. At this point, he provided written informed consent and a percutaneous core biopsy of a recurrent subcutaneous nodule on the chest was obtained. In order to determine possible mechanisms of resistance to PLX4032 in this tumor, the exons from 138 cancer genes from this sample were sequenced using massively parallel sequencing. The patient continued to have rapid progression of his disease and died on hospice in March 2010.

All exons from 138 cancer genes were sequenced from DNA isolated from both normal skin and the PLX4032-resistant tumor. Illumina sequencing libraries were generated from genomic DNA extracted from the patient's normal skin and resistant tumor specimen. Targeted hybrid capture of the genomic regions of interest were performed as previously described (Gnirke, A. et al. (2009) Nature Biotechnol. 27:182-189). Briefly, approximately 7000 biotinylated RNA baits corresponding to the coding sequence of 138 genes known to undergo somatic genomic alterations in cancer were designed and synthesized. Genomic DNA libraries were subjected to solution-phase hybrid capture with the biotinylated RNA baits followed by massively parallel sequencing. 36 bases from both ends of the samples were sequenced using an Illumina GAIIx. The sequencing data were deconvoluted to match all high-quality reads with the corresponding tumor samples and call base mutations, insertions, deletions, and copy number alterations.

A total of 14 somatic base substitutions were seen. Of these, 9 caused amino acid changes (non-synonymous), all of which were missense mutations. There were 5 silent (synonymous) substitutions. There were no insertions, deletions, or significant copy number alterations. The previously seen BRAF V600E mutation was again detected. In addition, amino acid changes in ERBB4, FLT1, MEK1, PTPRD, RET, RUNX1T1, and TERT were seen. To validate these 9 missense mutations, mass spectrometric genotypic assays to each somatic mutation seen in the tumor sample were designed. All 9 of the missense mutations were confirmed by mass spectrometric genotyping. In particular, mutations detected by massively parallel sequencing were tested for using multi-base hME extension chemistry by methods known in the art. To further confirm the sequencing results, the tumor DNA and normal DNA were also sequenced using a larger independent set targeting exons from approximately 2000 genes, and all 9 mutations were again seen.

Next, to determine if any of these mutations were de novo mutations that developed after the patient started PLX4032, the mass spectrometric genotypic assays were used to query the original pre-PLX4032 biopsy sample for the presence of these mutations. Two of the 9 missense mutations detected in the PLX4032-resistant tumor were not detected in the original PLX4032-sensitive tumor, suggesting that they were de novo somatic mutations. The first was a missense mutation (C121S) in MEK1, the kinase immediately downstream from BRAF, with a mutant allele frequency of 14%. The other was a missense mutation in RET with a mutant allele frequency of 28%.

It has previously been shown that mutations proximal to the C-helix of MEK1 can confer resistance to BRAF inhibition by PLX4032 by upregulating intrinsic MEK1 kinase activity (Emery, C. M. et al., (2009) Proc. Natl. Acad. Sci. USA 106:20411-20416). Therefore, it seemed plausible that the MEK1 C121 mutation, which is also located proximal to the C-helix, might have caused resistance to PLX4032 in the patient's recurrent tumor. To test this, the C121 S was introduced mutation into the sequence of wild-type MEK1 and the mutant cDNA was expressed in the A375 melanoma cell line, which harbors a BRAF V600E mutation. To introduce the C1212S mutation into the wild-type MEK1 sequence, MEK1 site-directed mutagenesis was performed as previously described (Emery, C. M. et al., (2009) Proc. Natl. Acad. Sci. USA 106:20411-20416). Briefly, MEK1 cDNA was amplified by PCR and site-directed mutagenesis was conducted using Quick-Change II (Stratagene) as per the manufacturer's instructions. As controls, the wild-type MEK1 sequence or a constitutively active variant of MEK1, referred to as MEK1-DD, was expressed in the A375 melanoma cells.

To examine the effect of the MEK1 C121 S mutation on responsiveness of the A375 melanoma cells to inhibitors, A375 cells (either untransfected cells, or cells transfected with either the wild-type MEK1, the C121S mutant MEK1, or the constitutively active variant MEK1-DD) were treated with increasing amounts of either the BRAF inhibitor PLX4720 (purchased from Symansis, Inc.), which is a compound closely related to PLX4032, or the MEK1 inhibitor AZD6244 (purchased from Selleck Chemical Co., Ltd.). The results are shown in the graphs of FIGS. 1A (PLX4720 treatment) and 1B (AZD6244 treatment).

As shown in FIG. 1A, cells expressing the MEK1 C121S mutation were strongly resistant to PLX4720, with 100-fold greater GI-50 values than wild-type A375 cells or A375 cells expressing wild-type MEK1 (MEK-WT). A375 cells expressing a constitutively active variant of MEK1 (MEK- DD) showed similar resistance to PLX4720 as MEK1 C121S. Similarly, as shown in FIG. 1B, cells expressing the MEK1 C121S mutation were strongly resistant to AZD6244, with nearly a 1000-fold greater GI-50 value than wild-type A375 cells, A375 cells expressing MEK-WT, and A375 cells expressing MEK-DD.

Figure 2A:
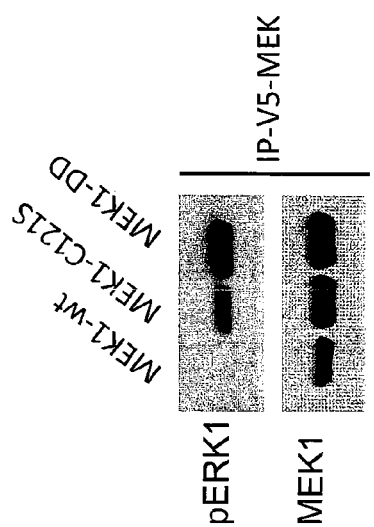
FIGS. 2A and 2B show the kinase activity of the MEK1 C121S mutant as compared wild-type MEK1 (MEK-WT) and a constitutively active MEK variant (MEK-DD).
Figure 2B:
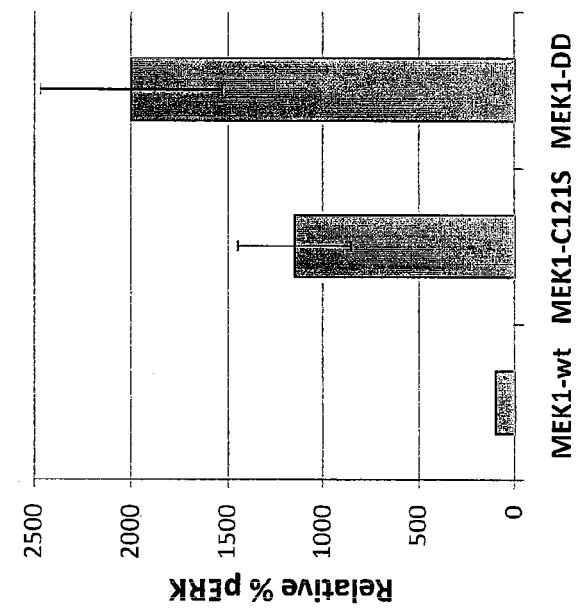

Biochemical evidence suggests that this resistance is indeed due to increased kinase activity of MEK1 C121S. To examine this, immunoblot studies were performed using standard procedures. Briefly, A375 melanoma cells were lysed with TNN buffer containing protease inhibitor (Roche), NaF and NaV0$_3$ (1 mM each). Lysates were quantified (Bradford assay), denatured (95° C.), and resolved by SDS gel electrophoresis. Protein was transferred to nitrocellulose membranes and probed with primary antibodies recognizing p-ERK1/2, p-MEK1/2 (Ser217/221), MEK1/2 and α-tubulin (Cell Signaling Technology; 1:1000 dilution). After incubation with the appropriate secondary antibody (anti-rabbit or anti-mouse IgG, HRP-linked; 1:1000 dilution) (Cell Signaling Technology), proteins were detected using chemiluminescence (Pierce). The results are summarized in FIGS. 2A and 2B, wherein FIG. 2A shows the immunoblot results and FIG. 2B is a graph quantitating the relative percentage of phosphorylated ERK1 (pERK1). As shown in FIGS. 2A and 2B, A375 cells expressing MEK1 C121S had higher levels of phosphorylated ERK1/2 as compared to A375 cells expressing MEK-WT. A375 cells expressing the constitutively active MEK1 variant MEK1-DD exhibited even higher levels of phosphorylated ERK1/2.

An in vitro kinase assay also demonstrated increased kinase activity of MEK1 C121S as compared to MEK1-WT. 293T cells at 70% confluency were transfected with 15 μg pc-DNA-DEST40 containing MEK-WT, MEK-DD, or MEK C121S. 48 hours post infection, lysate was generated and pull down with 40 ul of cobalt beads was performed for 30 mins at 4° C. on 1 mg of whole cell extract. Following pull down, in vitro kinase assays were performed as described previously (Emery, C. M. et al., (2009) *Proc. Natl. Acad. Sci. USA* 106:20411-20416).

In summary, a novel activating mutation in MEK1 has been identified, which arose de novo in a patient with BRAF-mutant metastatic melanoma who had developed resistance to the selective BRAF inhibitor PLX4032. The patient was initially highly responsive PLX4032, but after a dramatic 4-month response he developed rapid progression of disease. Analysis of a biopsy of the PLX4032-resistant tumor with massively parallel sequencing revealed a mutation in MEK1 (C121S) that was not detected in the pretreatment, PLX4032-sensitive biopsy sample. This mutation results in increased kinase activity and confers resistance to selective BRAF inhibition, as well as MEK1 inhibition, in vitro. Taken together, this suggests a mechanism by which this patient's tumor became resistant to BRAF inhibition.

A MEK1 mutation (P124L) that had arisen in a patient with metastatic melanoma who had developed resistance to the MEK1 inhibitor AZD6244 was previously described (Emery et al. (2009) supra). Like MEK1 C121S, MEK1 P124L mutation was proximal to the C-helix and conferred resistance to both the MEK1 inhibitor AZD6244 as well as the BRAF inhibitor PLX4720. A notable difference, however, is that the MEK1 C121S mutation seen here arose in the setting of BRAF inhibition rather than direct MEK1 inhibition.

Several mechanisms of acquired resistance to targeted kinase inhibition in patients have been described, the majority of which can be grouped into two categories. In the first category, secondary genomic alterations in the target kinase prevent access of the drug to the mutant kinase through various mechanisms while maintaining the oncogenic catalytic activity. These alterations are among the most common mechanisms of acquired resistance to kinase inhibitors and have been described in BCR-ABL, EGFR, and FLT3. The development of MEK1 P124L in response to MEK1 inhibition with AZD6244, as described in Emery et al. (2009) supra, is an example of this type of resistance mechanism. Notably, we did not detect any secondary mutations in BRAF in the PLX4032-resistant sample.

The second category involves genomic alterations in the target signaling pathway in genes other than the target of inhibition. These alterations compensate for the signals lost due to target inhibition, thereby "bypassing" inhibition of the target kinase. The best described example of this in patients is amplification of the MET oncogene, which has been observed in 20% of EGFR-mutant lung cancers with acquired resistance to gefitinib MET amplification leads to persistent activation of both PI3K/AKT and ERK signaling in the presence of EGFR inhibition. Other similar type mechanisms, including activation of IGF-1Rβ/IRS-1 signaling and signaling via the MET ligand HGF have also been described in cell lines with acquired resistance to targeted kinase inhibition.

The development of a MEK1 mutation in response to BRAF-inhibition represents the first reported example in a patient of an acquired resistance mechanism in which the tumor develops an activating mutation downstream of the target kinase. MEK1 C121S, in particular, adds an additional layer of complexity, as treatment with the BRAF inhibitor leads to acquisition of a genetic alteration which confers resistance to both the BRAF inhibitor as well as a MEK1 inhibitor. This has clinical significance when considering allosteric MEK1 inhibitors in patients who progress on PLX4032 or other BRAF inhibitors. Indeed, combination trials of combined PLX4032 and AZD6244 are now underway; the development of a MEK C121S or similar mutation might render a patient simultaneously resistant to both therapies. Overcoming resistance due to MEK1 C121S thus likely requires inhibition downstream of MEK1 or an alternative mechanism of inhibiting MEK1.

Reversion of the target kinase mutation to wildtype has not been described in patients treated with targeted kinase inhibitors, suggesting that cancers remain dependent on the original oncogenic mutations. Consistent with this, we detected continued presence of the V600E mutation. However, the BRAF mutation was detected at an allele frequency of 37%, which is lower than the expected 50%. Although this is likely this is due to "contamination" by normal DNA from surrounding stroma, we cannot rule out the possibility that a subset of the tumor cells lost the BRAF V600E mutation. One intriguing possibility is that tumor cells with the MEK1 C121S mutation (which was present at an allele frequency of 14%) no longer required BRAF V600E to activate the MAPK pathway. Supporting this idea, we have observed a reversion to BRAF wildtype in short term cultures derived from the AZD6244-resistant patient with metastatic melanoma with MEK1 P124L. Nevertheless, the fact that BRAF remains mutated at least in some subset of the cancer cells indicates that a preferred treatment approach is continued treatment with a BRAF inhibitor plus a second targeted therapy to overcome the resistance mutation.

EQUIVALENTS

The invention has been described herein with reference to certain examples and embodiments only. No effort has been made to exhaustively describe all possible examples and embodiments of the invention. Indeed, those of skill in the art will appreciate that various additions, deletions, modifications and other changes can be made to the above-described examples and embodiments, without departing from the intended spirit and scope of the invention as recited in the following claims. It is intended that all such additions, deletions, modifications and other changes be included within the scope of the following claims.

SUMMARY OF SEQUENCE LISTING

```
Wild-type Human MEK1 Nucleic Acid Sequence (NM_002755;
gi: 169790828)
[The start codon and the codon encoding amino acid position 121
are in bold and underlined]
                                                        SEQ ID NO: 1
aggcgaggct tccccttccc cgcccctccc ccggcctcca gtccctccca gggccgcttc gcagagcggc taggagcacg gcggcggcgg cactttcccc ggcaggagct ggagctgggc tctggtgcgc gcgcggctgt gccgcccgag ccggagggac tggttggttg agagagagag aggaagggaa tcccgggctg ccgaaccgca cgttcagccc gctccgctcc tgcagggcag cctttcggct ctctgcgcgc gaagccgagt cccgggcggg tggggcgggg gtccactgag accgctaccg gccccycgc gctgacggga ccgcgcgggg cgcacccgct gaaggcagcc ccggggcccg cggcccggac ttggtcctgc gcagcgggcg cggggcagcg cagcgggagg aagcgagagg tgctgccctc ccccggagt tggaagcgcg ttacccgggt ccaaaatgcc caagaagaag ccgacgccca tccagctgaa cccggccccc gacggctctg cagttaacgg gaccagctct gcggagacca acttggaggc cttgcagaag aagctggagg agctagagct tgatgagcag cagcgaaagc gccttgaggc ctttcttacc cagaagcaga aggtgggaga actgaaggat gacgactttg agaagatcag tgagctgggg gctggcaatg gcggtgtggt gttcaaggtc tcccacaagc cttctggcct ggtcatggcc agaaagctaa ttcatctgga gatcaaaccc gcaatccgga accagatcat aagggagctg caggttctgc atgagtgcaa ctctccgtac atcgtgggct tctatggtgc gttctacagc gatggcgaga tcagtatctg catggagcac atggatggag gttctctgga tcaagtcctg aagaaagctg gaagaattcc tgaacaaatt ttaggaaaag ttagcattgc tgtaataaaa ggcctgacat atctgaggga gaagcacaag atcatgcaca gagatgtcaa gccctccaac atcctagtca actcccgtgg ggagatcaag ctctgtgact ttggggtcag cgggcagctc atcgactcca tggccaactc cttcgtgggc acaaggtcct acatgtcgcc agaaagactc caggggactc attactctgt gcagtcagac atctggagca tgggactgtc tctggtagag atggcggttg ggaggtatcc catccctcct ccagatgcca aggagctgga gctgatgttt gggtgccagg tggaaggaga tgcggctgag accccaccca ggccaaggac ccccgggagg ccccttagct catacggaat ggacagccga cctcccatgg caattttga gttgttggat tacatagtca acgagcctcc tccaaaactg cccagtggag tgttcagtct ggaatttcaa gattttgtga ataaatgctt aataaaaaac cccgcagaga gagcagattt gaagcaactc atggttcatg cttttatcaa gagatctgat gctgaggaag tggattttgc aggttggctc tgctccacca tcggccttaa ccagcccagc acaccaaccc atgctgctgg cgtctaagtg tttgggaagc aacaaagagc gagtcccctg cccggtggtt tgccatgtcg cttttgggcc tccttcccat gcctgtctct gttcagatgt gcatttcacc tgtgacaaag gatgaagaac acagcatgtg ccaagattct actcttgtca tttttaatat tactgtcttt attcttatta ctattattgt tccctaagt ggattggctt tgtgcttggg gctatttgtg tgtatgctga tgatcaaaac ctgtgccagg ctgaattaca gtgaaatttt ggtgaatgtg ggtagtcatt cttacaattg cactgctgtt cctgctccat gactggctgt ctgcctgtat tttcgggatt cttgtcatt tggtggtact ttattcttgc tgggcatact ttctctctag gagggagcct tgtgagatcc ttcacaggca
```

-continued

```
gtgcatgtga agcatgcttt gctgctatga aaatgagcat cagagagtgt acatcatgtt attttattat tattatttgc ttttcatgta gaactcagca gttgacatcc aaatctagcc agagcccttc actgccatga tagctggggc ttcaccagtc tgtctactgt ggtgatctgt agacttctgg ttgtatttct atatttattt tcagtatact gtgtgggata cttagtggta tgtctcttta agttttgatt aatgtttctt aaatggaatt attttgaatg tcacaaattg atcaagatat taaaatgtcg gatttatctt tccccatatc caagtaccaa tgctgttgta aacaacgtgt atagtgccta aaattgtatg aaaatccttt taaccatttt aacctagatg tttaacaaat ctaatctctt attctaataa atatactatg aaataaaaaa aaaaggatga aagctaaaaa aaaaaaaaaa aaa
```

Wild-type Human MEK1 Amino Acid Sequence (NP_002746; gi: 5579478)
[Cysteine at amino acid position 121 is in bold and underlined]
SEQ ID NO: 2

```
mpkkkptpiq lnpapdgsav ngtssaetnl ealqkkleel eldeqqrkrl eafltqkqkv gelkdddfek iselgagngg vvfkvshkps glvmarklih leikpairnq iirelqvlhe cnspyivgfy gafysdgeis icmehmdggs ldqvlkkagr ipeqilgkvs iavikgltyl rekhkimhrd vkpsnilvns rgeiklcdfg vsgqlidsma nsfvgtrsym sperlqgthy svqsdiwsmg lslvemavgr ypippppdake lelmfgcqve gdaaetpprp rtpgrplssy gmdsrppmai felldyivne pppklpsgvf slefqdfvnk cliknpaera dlkqlmvhaf ikrsdaeevd fagwlcstig lnqpstptha agv
```

Mutant MEK1 C121S Nucleic Acid Sequence
[The start codon and the codon encoding amino acid position 121
are in bold and underlined; n = a, c, g or t]
SEQ ID NO: 3

```
aggcgaggct tcccctttccc cgcccctccc ccggcctcca gtccctccca gggccgcttc gcagagcggc taggagcacg gcggcggcgg cactttcccc ggcaggagct ggagctgggc tctggtgcgc gcgcggctgt gccgcccgag ccggagggac tggttggttg agagagagag aggaagggaa tcccgggctg ccgaaccgca cgttcagccc gctccgctcc tgcagggcag cctttcggct ctctgcgcgc gaagccgagt cccgggcggg tggggcgggg gtccactgag accgctaccg gccgctcggc gctgacggga ccgcgcgggg cgcacccgct gaaggcagcc ccggggcccg cggcccggac ttggtcctgc gcagcgggcg cggggcagcg cagcgggagg aagcgagagg tgctgccctc ccccggagt tggaagcgcg ttacccgggt ccaaaatgcc caagaagaag ccgacgccca tccagctgaa cccggccccc gacggctctg cagttaacgg gaccagctct gcggagacca acttggaggc cttgcagaag aagctggagg agctagagct tgatgagcag cagcgaaagc gccttgaggc ctttcttacc cagaagcaga aggtgggaga actgaaggat gacgactttg agaagatcag tgagctgggg gctggcaatg gcggtgtggt gttcaaggtc tcccacaagc cttctggcct ggtcatggcc agaaagctaa tcatctgga gatcaaaccc gcaatccgga accagatcat aagggagctg caggttctgc atgagtcnaa ctctccgtac atcgtgggct tctatggtgc gttctacagc gatggcgaga tcagtatctg catggagcac atggatggag ttctctgga tcaagtcctg aagaaagctg gaagaattcc tgaacaaatt ttaggaaaag ttagcattgc tgtaataaaa ggcctgacat atctgaggga gaagcacaag atcatgcaca gagatgtcaa gccctccaac atcctagtca actcccgtgg ggagatcaag ctctgtgact tggggtcag cgggcagctc atcgactcca tggccaactc cttcgtgggc acaaggtcct acatgtcgcc agaaagactc cagggggactc attactctgt gcagtcagac atctggagca tgggactgtc tctggtagag atggcggttg ggaggtatcc
```

```
catccctcct ccagatgcca aggagctgga gctgatgttt gggtgccagg tggaaggaga tgcggctgag accccaccca ggccaaggac ccccggagg cccccttagct catacggaat ggacagccga cctcccatgg caattttttga gttgttggat tacatagtca acgagcctcc tccaaaactg cccagtggag tgttcagtct ggaatttcaa gattttgtga ataaatgctt aataaaaaac cccgcagaga gagcagattt gaagcaactc atggttcatg cttttatcaa gagatctgat gctgaggaag tggattttgc aggttggctc tgctccacca tcggccttaa ccagcccagc acaccaaccc atgctgctgg cgtctaagtg tttgggaagc aacaaagagc gagtcccctg cccggtggtt tgccatgtcg cttttgggcc tccttcccat gcctgtctct gttcagatgt gcatttcacc tgtgacaaag gatgaagaac acagcatgtg ccaagattct actcttgtca ttttttaatat tactgtcttt attcttatta ctattattgt tcccctaagt ggattggctt tgtgcttggg gctatttgtg tgtatgctga tgatcaaaac ctgtgccagg ctgaattaca gtgaaatttt ggtgaatgtg ggtagtcatt cttacaattg cactgctgtt cctgctccat gactggctgt ctgcctgtat tttcgggatt ctttgacatt tggtggtact ttattcttgc tgggcatact ttctctctag agggagcct tgtgagatcc ttcacaggca gtgcatgtga agcatgcttt gctgctatga aaatgagcat cagagagtgt acatcatgtt atttttattat tattatttgc ttttcatgta gaactcagca gttgacatcc aaatctagcc agagcccttc actgccatga tagctggggc ttcaccagtc tgtctactgt ggtgatctgt agacttctgg ttgtatttct atatttattt tcagtatact gtgtgggata cttagtggta tgtctcttta agttttgatt aatgtttctt aaatggaatt atttttgaatg tcacaaattg atcaagatat taaaatgtcg gatttatctt tccccatatc caagtaccaa tgctgttgta aacaacgtgt atagtgccta aaattgtatg aaaatccttt taaccatttt aacctagatg tttaacaaat ctaatctctt attctaataa atatactatg aaataaaaaa aaaaggatga aagctaaaaa aaaaaaaaaa aaa
```

Mutant MEK1 C121S Amino Acid Sequence
[Serine at amino acid position 121 is in bold and underlined]

SEQ ID NO: 4

```
mpkkkptpiq lnpapdgsav ngtssaetnl ealqkkleel eldeqqrkrl eafltqkqkv gelkdddfek iselgagngg vvfkvshkps glvmarklih leikpairnq iirelqvlhe snspyivgfy gafysdgeis icmehmdggs ldqvlkkagr ipeqilgkvs iavikgltyl rekhkimhrd vkpsnilvns rgeiklcdfg vsgqlidsma nsfvgtrsym sperlqgthy svqsdiwsmg lslvemavgr ypipppdake lelmfgcqve gdaaetpprp rtpgrplssy gmdsrppmai felldyivne pppklpsgvf slefqdfvnk cliknpaera dlkqlmvhaf ikrsdaeevd fagwlcstig lnqpstptha agv
```

What is claimed:

1. A method of identifying a compound effective for inhibiting a mutant MEK1 protein activity, the mutant MEK1 protein having a C121S amino acid substitution, the method comprising:
   (a) providing an assay composition comprising:
      a mutant MEK1 protein having MEK1 activity, the mutant MEK1 protein comprising an amino acid substitution at position 121 of wild-type MEK1 protein shown in SEQ ID NO: 2 where the amino acid substitution is a C121S amino acid substitution that confers resistance to one or more RAF or MEK inhibitors on a cell expressing the mutant MEK1 protein, wherein the RAF inhibitor is selected from PLX4720 or PLX4032 and wherein the MEK inhibitor is AZD624; and
   a MEK substrate;
   (b) contacting the assay composition with a test compound under conditions that permit phosphorylation of the MEK substrate in the absence of the test compound; and
   (c) determining the effect of the compound on phosphorylation of the MEK substrate;
   wherein down-modulation of phosphorylation of the MEK substrate as compared to the mutant MEK1 protein not treated with the test compound identifies the test compound as a compound effective for inhibiting the mutant MEK1 protein activity having the C121S amino acid substitution.

2. The method of claim 1, wherein the MEK substrate is ERK1/2.

3. The method of claim 1, wherein the assay composition is a cell extract or a purified protein.

* * * * *

SEQUENCE LISTING

<160> NUMBER OF SEQ ID NOS: 4

<210> SEQ ID NO 1
<211> LENGTH: 2603
<212> TYPE: DNA
<213> ORGANISM: Homo sapiens

<400> SEQUENCE: 1

```
aggcgaggct tccccttccc cgcccctccc ccggcctcca gtccctccca gggccgcttc    60
gcagagcggc taggagcacg gcggcggcgg cactttcccc ggcaggagct ggagctgggc   120
```

```
tctggtgcgc gcgcggctgt gccgcccgag ccggagggac tggttggttg agagagagag      180
aggaagggaa tcccgggctg ccgaaccgca cgttcagccc gctccgctcc tgcagggcag      240
cctttcggct ctctgcgcgc gaagccgagt cccgggcggg tggggcgggg gtccactgag      300
accgctaccg gccccctcggc gctgacggga ccgcgcgggg cgcacccgct gaaggcagcc     360
ccggggcccg cggcccggac ttggtcctgc gcagcgggcg cggggcagcg cagcgggagg      420
aagcgagagg tgctgccctc ccccggagt tggaagcgcg ttacccgggt ccaaaatgcc       480
caagaagaag ccgacgccca tccagctgaa cccggccccc gacggctctg cagttaacgg      540
gaccagctct gcggagacca acttggaggc cttgcagaag aagctggagg agctagagct      600
tgatgagcag cagcgaaagc gccttgaggc ctttcttacc cagaagcaga aggtgggaga     660
actgaaggat gacgactttg agaagatcag tgagctgggg gctggcaatg gcggtgtggt     720
gttcaaggtc tcccacaagc cttctggcct ggtcatggcc agaaagctaa ttcatctgga     780
gatcaaaccc gcaatccgga accagatcat aagggagctg caggttctgc atgagtgcaa     840
ctctccgtac atcgtgggct ctatggtgc gttctacagc gatggcgaga tcagtatctg       900
catggagcac atggatggag gttctctgga tcaagtcctg aagaaagctg aagaattcc       960 tgaacaaatt ttaggaaaag ttagcattgc tgtaataaaa ggcctgacat atctgaggga    1020
gaagcacaag atcatgcaca gagatgtcaa gccctccaac atcctagtca actcccgtgg    1080
ggagatcaag ctctgtgact ttggggtcag cgggcagctc atcgactcca tggccaactc    1140
cttcgtgggc acaaggtcct acatgtcgcc agaaagactc cagggactc attactctgt      1200 gcagtcagac atctggagca tgggactgtc tctggtagag atggcggttg ggaggtatcc    1260
catccctcct ccagatgcca aggagctgga gctgatgttt gggtgccagg tgaaggaga     1320 tgcggctgag accccaccca ggccaaggac ccccgggagg cccttagct catacggaat     1380 ggacagccga cctcccatgg caatttttga gttgttggat tacatagtca acgagcctcc    1440
tccaaaactg cccagtggag tgttcagtct ggaatttcaa gattttgtga ataaatgctt    1500
aataaaaaac cccgcagaga gagcagattt gaagcaactc atggttcatg cttttatcaa     1560
gagatctgat gctgaggaag tggattttgc aggttggctc tgctccacca tcggccttaa    1620
ccagcccagc acaccaaccc atgctgctgg cgtctaagtg tttgggaagc aacaaagagc    1680
gagtcccctg cccggtggtt tgccatgtcg cttttgggcc tccttcccat gcctgtctct    1740
gttcagatgt gcatttcacc tgtgacaaag gatgaagaac acagcatgtg ccaagattct   1800
actcttgtca ttttaatat tactgtcttt attcttatta ctattattgt tcccctaagt    1860
ggattggctt tgtgcttggg gctatttgtg tgtatgctga tgatcaaaac ctgtgccagg    1920
ctgaattaca gtgaaatttt ggtgaatgtg ggtagtcatt cttacaattg cactgctgtt    1980
cctgctccat gactggctgt ctgcctgtat tttcgggatt cttttgacatt tggtggtact  2040 ttattcttgc tgggcatact ttctctctag gagggagcct tgtgagatcc ttcacaggca    2100
gtgcatgtga agcatgcttt gctgctatga aaatgagcat cagagagtgt acatcatgtt    2160 atttttattat tattatttgc ttttcatgta gaactcagca gttgacatcc aaatctagcc   2220
agagcccttc actgccatga tagctggggc ttcaccagtc tgtctactgt ggtgatctgt    2280
agacttctgg ttgtatttct atatttattt tcagtatact gtgtgggata cttagtggta     2340
tgtctcttta agttttgatt aatgtttctt aaatggaatt attttgaatg tcacaaattg    2400
atcaagatat taaaatgtcg gatttatctt tccccatatc caagtaccaa tgctgttgta    2460
```

```
aacaacgtgt atagtgccta aaattgtatg aaaatccttt taaccatttt aacctagatg    2520
tttaacaaat ctaatctctt attctaataa atatactatg aataaaaaaa aaaaggatga    2580
aagctaaaaa aaaaaaaaaa aaa                                             2603
```

<210> SEQ ID NO 2
<211> LENGTH: 393
<212> TYPE: PRT
<213> ORGANISM: Homo sapiens

<400> SEQUENCE: 2

```
Met Pro Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350
```

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390

<210> SEQ ID NO 3
<211> LENGTH: 2603
<212> TYPE: DNA
<213> ORGANISM: Homo sapiens
<220> FEATURE:
<221> NAME/KEY: misc_feature
<222> LOCATION: (838)..(838)
<223> OTHER INFORMATION: n is a, c, g, or t

<400> SEQUENCE: 3

| | | | | | |
|---|---|---|---|---|---|
| aggcgaggct | tccccttccc | cgcccctccc | ccggcctcca | gtccctccca | gggccgcttc | 60 |
| gcagagcggc | taggagcacg | gcggcggcgg | cactttcccc | ggcaggagct | ggagctgggc | 120 |
| tctggtgcgc | gcgcggctgt | gccgcccgag | ccggagggac | tggttggttg | agagagagag | 180 |
| aggaagggaa | tcccgggctg | ccgaaccgca | cgttcagccc | gctccgctcc | tgcagggcag | 240 |
| cctttcggct | ctctgcgcgc | gaagccgagt | cccgggcggg | tggggcgggg | gtccactgag | 300 |
| accgctaccg | gccctcggc | gctgacggga | ccgcgcgggg | cgcacccgct | gaaggcagcc | 360 |
| ccggggcccg | cggccggac | ttggtcctgc | gcagcgggcg | cggggcagcg | cagcgggagg | 420 |
| aagcgagagg | tgctgccctc | cccccggagt | tggaagcgcg | ttacccgggt | ccaaaatgcc | 480 |
| caagaagaag | ccgacgccca | tccagctgaa | cccggccccc | gacggctctg | cagttaacgg | 540 |
| gaccagctct | gcggagacca | acttggaggc | cttgcagaag | aagctggagg | agctagagct | 600 |
| tgatgagcag | cagcgaaagc | gccttgaggc | cttctcttacc | cagaagcaga | aggtgggaga | 660 |
| actgaaggat | gacgactttg | agaagatcag | tgagctgggg | gctggcaatg | gcggtgtggt | 720 |
| gttcaaggtc | tcccacaagc | cttctggcct | ggtcatggcc | agaaagctaa | ttcatctgga | 780 |
| gatcaaaccc | gcaatccgga | accagatcat | aagggagctg | caggttctgc | atgagtcnaa | 840 |
| ctctccgtac | atcgtgggct | tctatggtgc | gttctacagc | gatggcgaga | tcagtatctg | 900 |
| catggagcac | atggatggag | ttctctctgga | tcaagtcctg | aagaaagctg | aagaattcc | 960 |
| tgaacaaatt | ttaggaaaag | ttagcattgc | tgtaataaaa | ggcctgacat | atctgaggga | 1020 |
| gaagcacaag | atcatgcaca | gagatgtcaa | gccctccaac | atcctagtca | actcccgtgg | 1080 |
| ggagatcaag | ctctgtgact | ttggggtcag | cgggcagctc | atcgactcca | tggccaactc | 1140 |
| cttcgtgggc | acaaggtcct | acatgtcgcc | agaaagactc | cagggactc | attactctgt | 1200 |
| gcagtcagac | atctggagca | tgggactgtc | tctggtagag | atggcggttg | ggaggtatcc | 1260 |
| catccctcct | ccagatgcca | aggagctgga | gctgatgttt | gggtgccagg | tggaaggaga | 1320 |
| tgcggctgag | accccaccca | ggccaaggac | ccccgggagg | cccctttagct | catacggaat | 1380 |
| ggacagccga | cctcccatgg | caattttttga | gttgttggat | tacatagtca | acgagcctcc | 1440 |
| tccaaaactg | cccagtggag | tgttcagtct | ggaatttcaa | gattttgtga | ataaatgctt | 1500 |
| aataaaaaac | cccgcagaga | gagcagattt | gaagcaactc | atggttcatg | cttttatcaa | 1560 |
| gagatctgat | gctgaggaag | tggattttgc | aggttggctc | tgctccacca | tcggccttaa | 1620 |
| ccagcccagc | acaccaaccc | atgctgctgg | cgtctaagtg | tttgggaagc | aacaaagagc | 1680 |
| gagtcccctg | cccggtggtt | tgccatgtcg | cttttgggcc | tccttcccat | gcctgtctct | 1740 |

```
gttcagatgt gcatttcacc tgtgacaaag gatgaagaac acagcatgtg ccaagattct   1800
actcttgtca ttttaatat tactgtcttt attcttatta ctattattgt tcccctaagt    1860
ggattggctt tgtgcttggg gctatttgtg tgtatgctga tgatcaaaac ctgtgccagg   1920
ctgaattaca gtgaaatttt ggtgaatgtg ggtagtcatt cttacaattg cactgctgtt   1980
cctgctccat gactggctgt ctgcctgtat tttcgggatt ctttgacatt tggtggtact   2040
ttattcttgc tgggcatact ttctctctag gagggagcct tgtgagatcc ttcacaggca   2100
gtgcatgtga agcatgcttt gctgctatga aaatgagcat cagagagtgt acatcatgtt   2160
attttattat tattatttgc ttttcatgta gaactcagca gttgacatcc aaatctagcc   2220
agagcccttc actgccatga tagctggggc ttcaccagtc tgtctactgt ggtgatctgt   2280
agacttctgg ttgtatttct atatttattt tcagtatact gtgtgggata cttagtggta   2340
tgtctcttta agttttgatt aatgtttctt aaatggaatt attttgaatg tcacaaattg   2400
atcaagatat taaatgtcg gatttatctt tccccatatc caagtaccaa tgctgttgta    2460
aacaacgtgt atagtgccta aaattgtatg aaaatccttt taaccatttt aacctagatg   2520
tttaacaaat ctaatctctt attctaataa atatactatg aaataaaaaa aaaaggatga   2580
aagctaaaaa aaaaaaaaaa aaa                                           2603
```

<210> SEQ ID NO 4
<211> LENGTH: 393
<212> TYPE: PRT
<213> ORGANISM: Homo sapiens

<400> SEQUENCE: 4

```
Met Pro Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Ser Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
```

```
                210                 215                 220
Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
                260                 265                 270

Leu Met Phe Gly Cys Gln Val Glu Gly Asp Ala Ala Glu Thr Pro Pro
                275                 280                 285

Arg Pro Arg Thr Pro Gly Arg Pro Leu Ser Ser Tyr Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
                355                 360                 365

Val Asp Phe Ala Gly Trp Leu Cys Ser Thr Ile Gly Leu Asn Gln Pro
                370                 375                 380

Ser Thr Pro Thr His Ala Ala Gly Val
385                 390
```